(12) United States Patent
Corwin et al.

(10) Patent No.: US 11,597,960 B2
(45) Date of Patent: Mar. 7, 2023

(54) ASSESSMENT OF MICRO-ORGANISM PRESENCE

(71) Applicant: General Electric Company, Schenectady, NY (US)

(72) Inventors: Alex David Corwin, Niskayuna, NY (US); Erik Leeming Kvam, Niskayuna, NY (US); Christine Lynne Surrette, Niskayuna, NY (US); Brian Joseph Scherer, Niskayuna, NY (US); Pei-Hsin Kuo, Schenectady, NY (US); Ralf Lenigk, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 918 days.

(21) Appl. No.: 16/459,336

(22) Filed: Jul. 1, 2019

(65) Prior Publication Data
US 2021/0002688 A1    Jan. 7, 2021

(51) Int. Cl.
*C12Q 1/14*    (2006.01)
*C12Q 1/04*    (2006.01)
(Continued)

(52) U.S. Cl.
CPC ............. *C12Q 1/04* (2013.01); *C12M 23/16* (2013.01); *C12Q 1/06* (2013.01); *C12M 23/12* (2013.01);
(Continued)

(58) Field of Classification Search
CPC ...... C12M 23/16; C12M 23/12; C12M 23/24; C12M 41/00; C12Q 1/06; G01N 21/01;
(Continued)

(56) References Cited

U.S. PATENT DOCUMENTS 5,501,959 A    3/1996  Lancaster et al.
5,780,866 A *  7/1998  Yamamura ........... G01N 21/956
                                                250/559.22
(Continued)

FOREIGN PATENT DOCUMENTS

JP    2002537579 A  *  2/2000
JP    2018087770 A  *  6/2018
(Continued)

OTHER PUBLICATIONS

Sarker, Satyajit D., et al.; "Microtitre plate-based antibacterial assay incorporating resazurin as an indicator of cell growth, and its application in the in vitro antibacterial screening of phytochemicals", Methods, vol. 42, Issue: 04, pp. 321-324, Sep. 2007.
(Continued)

*Primary Examiner* — Michael A Lyons
*Assistant Examiner* — Omar H Nixon
(74) *Attorney, Agent, or Firm* — Fletcher Yoder, P.C.

(57) ABSTRACT

The present disclosure relates to approaches for assessing a sample or the presence of microorganisms. The sample, in certain implementations may be assessed for one or both of absence of microorganisms (sterility) and/or for concentration of said organisms (bio-burden). sample partition device may be employed that partitions the sample input volume into multiple discrete measurement zones with little or no loss of sample (e.g., zero-loss) and with little operator involvement, thereby reducing operator- and environment-based false positives.

20 Claims, 14 Drawing Sheets

(51) Int. Cl.
*C12M 3/06* (2006.01)
*C12Q 1/06* (2006.01)
*C12M 1/32* (2006.01)
*C12M 1/34* (2006.01)
*C12M 1/00* (2006.01)
*C12M 1/04* (2006.01)
*G01N 21/01* (2006.01)
*G06T 7/00* (2017.01)

(52) U.S. Cl.
CPC .............. *C12M 23/24* (2013.01); *C12M 23/34* (2013.01); *C12M 41/00* (2013.01); *G01N 21/01* (2013.01); *G06T 7/0008* (2013.01); *G06T 7/0012* (2013.01); *G06T 2207/30024* (2013.01)

(58) Field of Classification Search
CPC ................. G06T 7/0008; G06T 7/0012; G06T 2207/30024
USPC ........................................................... 435/35
See application file for complete search history.

(56) References Cited

U.S. PATENT DOCUMENTS

| | | |
|---|---|---|
| 7,282,348 B2 | 10/2007 | Riss et al. |
| 7,341,841 B2 | 3/2008 | Metzger et al. |
| 7,354,774 B2 | 4/2008 | Hughes et al. |
| 8,641,987 B2 | 2/2014 | Sandell |
| 9,274,101 B2 | 3/2016 | Bochner et al. |
| 9,562,253 B1 | 2/2017 | Turner |
| 9,642,858 B2 | 5/2017 | Horzempa et al. |
| 9,677,109 B2 * | 6/2017 | Shamsheyeva ... B01L 3/502715 |
| 9,909,162 B2 | 3/2018 | Yeh |
| 10,012,640 B2 | 7/2018 | Pant et al. |
| 10,161,948 B2 | 12/2018 | Vacic et al. |
| 2008/0063257 A1* | 3/2008 | Hiroi .......................... G03F 1/86 382/149 |
| 2009/0297007 A1* | 12/2009 | Cosatto ................. G06T 7/0012 382/131 |
| 2016/0047816 A1 | 2/2016 | Stern et al. |
| 2016/0054303 A1 | 2/2016 | Hanson |
| 2016/0289729 A1 | 10/2016 | Richards et al. |
| 2016/0354777 A1 | 12/2016 | Chiu et al. |
| 2017/0051238 A1 | 2/2017 | Tanaka et al. |
| 2018/0014876 A1 | 1/2018 | Allen, IV |

FOREIGN PATENT DOCUMENTS

| | | |
|---|---|---|
| WO | 0198531 A1 | 12/2001 |
| WO | 2018021281 A1 | 2/2018 |

OTHER PUBLICATIONS

Hsieh, Kuangwen, et al.; "Simple and precise counting of viable bacteria by resazurin-amplified picoarray detection", Analytical Chemistry, vol. 90, Issue: 15, pp. 9449-9456, Jul. 3, 2018.

* cited by examiner

Time-to-detection (hrs)

| | 1 | 2 | 3 | 4 | 5 | 6 | 7 | 8 | 9 | 10 | 11 | 12 | |
|---|---|---|---|---|---|---|---|---|---|---|---|---|---|
| A | 21 | 22 | AIR | AIR | AIR | 24 | | | | | | | Inlet |
| B | | | | 23 | | | | | | | | | |
| C | | | 19 | | | | | | | | 18 | 21 | |
| D | 24 | 23 | 20 | 22 | 24 | | | | 23 | | 20 | | |
| E | | | 19 | 22 | 20 | | | | | | | | |
| F | | | | | | | 21 | 23 | | | | | |
| G | AIR | | | | | | | | | | | | |
| H | AIR | | | | | 22 | | | | | | | |
| I | AIR | | 21 | | | | | | 23 | | 21 | | |
| J | AIR | | | | | | AIR | | | | | | |
| | Outlet | | | | | | | | | | | Total | |
| | 2 | 2 | 5 | 3 | 2 | 2 | 1 | 1 | 2 | 0 | 3 | 1 | 24 |

| TTD AVE | STDEV | FALSE positive | EXPECTED (for 1 E. coli per well) |
|---|---|---|---|
| 21.54167 | 1.667572 | 0 | 20 |

FIG. 15

ASSESSMENT OF MICRO-ORGANISM PRESENCE

TECHNICAL FIELD

The subject matter disclosed herein relates to micro-organism testing.

BACKGROUND

In various contexts it may be desirable to test a sample (e.g., a drug, water, or food sample) for the presence of microorganisms (e.g., bacteria, yeast, mold, and so forth). Such tests may involve testing for the presence of any micro-organisms (i.e., sterility) or for the presence of an acceptable threshold amount of a micro-organism (i.e., bio-burden).

Existing testing processes for sterility and bio-burden, however, may be relatively slow, (e.g., 714 days). The slowness of these processes may be driven by several factors including low assay sensitivity, room-temperature incubation to avoid temperature-sensitive bias, and end-point interpretation due to lack of real-time feedback over the incubation interval. In addition, current testing processes may be subject to numerous manual steps leading to low throughput. This low throughput may be driven by, for example, sample preparation requirements associated with filtering and/or diluting and culturing the sample with appropriate controls to detect operator-based and environment-based false positives. In addition, test results may be difficult to track in certain settings due to manual interfaces with the laboratory information management system (LIMS) in these settings. Lastly, currently employed compendial methods involve manual inspection and interpretation of cell growth in liquid or agar plate cultures. Such manual and labor intensive processes may result in a time-consuming testing process, which may delay corrective action in a manufacturing context or other time-sensitive context.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a cell analysis system is provided. In accordance with this embodiment, the cell analysis system comprises an imaging sub-system configured to automatically acquire successive images and a processing sub-system configured control operation of the imaging sub-system and to process data acquired using the imaging sub-system. The imaging sub-system and processing sub-system in cooperation perform acts comprising: measuring a fill height of each sample-containing well of a plurality of wells of a well plate, wherein the sample-containing wells contain a sample that is partitioned between the sample-containing wells; determining a focal plane height for each sample-containing well based at least in part on the respective fill height of sample within each sample-containing well; acquiring, using the focal plane height determined for each sample-containing well, successive images of the respective sample-containing well; determining, using the acquired successive images, a change in a measured optical parameter at each sample-containing well over time relative to a baseline; and generating an assessment of micro-organism presence within the sample based on the determined changes in the measured optical parameter at each sample-containing well over time.

In a further embodiment, a method for assessing micro-organism presence within a sample is provided. In accordance with this method, a sample is partitioned between a plurality of wells of a well plate to form a plurality of sample-containing wells. A fill height of each sample-containing well of the plurality of sample-containing is measured. A focal plane height is determined for each sample-containing well based at least in part on the respective fill height of sample within each sample-containing well. Using the focal plane height determined for each sample-containing well, successive images are acquired of the respective sample-containing wells. Using the acquired successive images, a change in a measured optical parameter at each sample-containing well over time is determined relative to a baseline. An assessment of micro-organism presence within the sample is generated based on the determined changes in the measured optical parameter at each sample-containing well over time.

In an additional embodiment, a method for assessing analyzing a well plate is provided. In accordance with this embodiment, a sample is partitioned between a plurality of wells of a well plate to form a plurality of sample-containing wells. A fill height of each sample-containing well of the plurality of sample-containing is measured. An assessment is generated of micro-organism presence within the sample based on images acquired over time of the sample-containing wells at, for each sample containing well, a respective focal plane height determined based at least in part on the respective fill height of each sample-containing well.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 15 graphically depicts time-to-detection of micro-organism growth in wells of a sample partition device, in accordance with aspects of the present disclosure;

DETAILED DESCRIPTION

Figure 1:
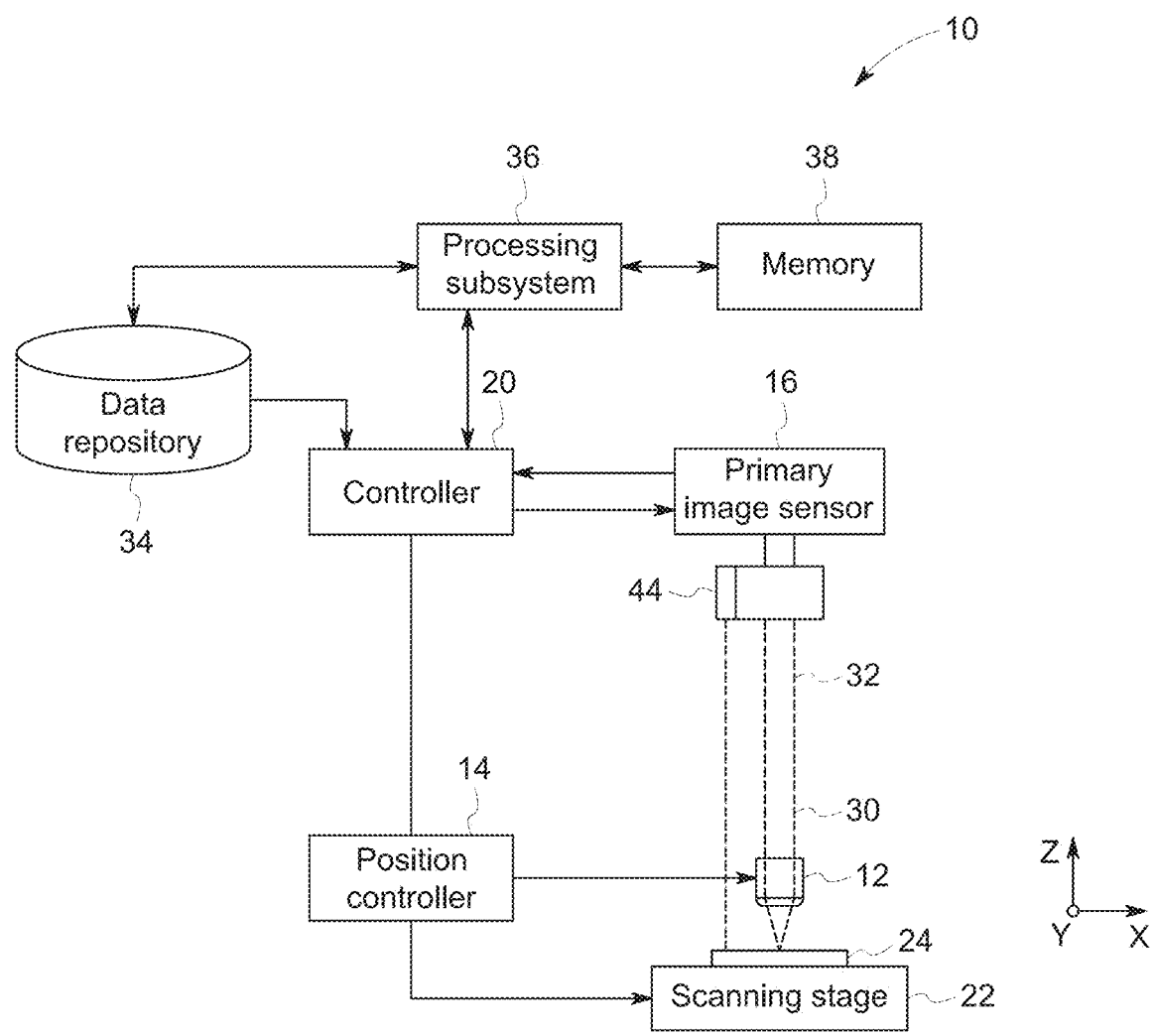
FIG. 1 is a block diagram of an imaging system, such as a digital optical microscope system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

With this in mind, and as discussed herein, the present disclosure relates to a workflow and system suitable for assessing one or both of sterility and bio-burden with respect to a sample (e.g., a drug, food, or water sample). In certain implementations, the sample loaded into a partitioning device as described herein is a mixture of a substance to be tested (e.g., a food, drug, and so forth) and microbial culture media, such as (but not limited to) tryptic soy broth, Sabouraud dextrose broth, soybean-casein digest medium, fluid thioglycollate medium, potato-dextrose broth, or Schaedler Broth. In further embodiments, a metabolic dye or oxidation-reduction indicator is formulated with the microbial culture media The present technique helps address current issues related to sterility and bio-burden testing, such as issues related to labor and time intensity. In particular, such issues with current techniques include, but are not limited to: low assay sensitivity, room-temperature incubation to avoid temperature-sensitive bias, and end-point interpretation due to lack of real-time feedback. In addition, current testing processes may also be subject to numerous manual steps leading to low throughput.

Various challenges exist to improving the wait-time associated with current sterility and bio-burden testing methodologies. First, certain known rapid microbial methods are critically dependent on filtration during sample preparation, and are therefore incompatible with samples that foul during filtration, making such techniques incompatible with non-filterable samples. Second, some existing techniques are not growth based and therefore may detect cells that are non-viable, leading to false-positive sensing of "viable but non-culturable" phenotypes. Lastly, other rapid microbial methods may have rapid detection, but complicated or slow sample preparation (e.g., too many handling steps).

In contrast, the presently contemplated techniques provide for relatively rapid testing for micro-organism presence and/or concentration in a sample without being subject to these issues. In certain aspects, an easy to load, sterile, consumable device (i.e., a sample partition device) is provided for use with a microscope imager and integrated analytical software. In certain implementations, the sample partition device may be pre-assembled or pre-packaged in a closed, sterile state which can then be loaded with a sample in a non-sterile environment. This may be in contrast to other approaches in which a sample holding device is loaded in an open state and sealed or closed once the sample is loaded, which precludes loading in a non-sterile environment.

Using the presently contemplated sample partition device, a sample can be tested either for presence or absence of microorganisms (sterility) and/or for concentration of said organisms (bio-burden). All of the sample may be contained in the sample partition device, and the device may be employed with both filterable and non-filterable samples, including those containing human or other animal (or plant) cells. For example, use of the present sample partition device and/or micro-organism growth methodology may allow bright field detection of microbes in the presence of human cells (which is one example of a non-filterable drug like cell therapy). The sample partition device partitions the sample input volume into multiple discrete measurement zones with little or no loss of sample (e.g., zero-loss) and with little operator involvement, thereby reducing operator- and environment-based false positives. In practice, the sample partition device may be sized to accommodate any suitable total process volume, such as total process volumes between 5 mL and 200 mL, or larger as needed. In one embodiment, the primary filling mechanism of the wells of the sample partition device does not employ capillary action and the device does not include microfluidic flow paths or features, where microfluidic flow paths or features are understood to be those paths of less than 1,000 microns in a cross-sectional dimension.

Detection of micro-organisms (e.g., bacteria, yeast, mold, and so forth) may be performed via one or both of fluorescent microscopy or bright field (transmission) microscopy, and allows for real-time determination of the presence or absence of micro-organisms. In one embodiment, detection by fluorescent microscopy involves a metabolic dye or oxidation-reduction indicator, which includes but is not limited to resazurin. Detection may be performed through a series of observations (e.g., pixel intensity or color measurements) at fixed (or variable) time intervals. Where suitable, an appropriate imaging metric may be applied to the measurements to determine if micro-organisms are present. In this manner, data may be generated over the course of an incubation interval, and not simply at an endpoint.

With the preceding discussion in mind, FIG. 1 illustrates an embodiment of an automated digital microscopy system 10 that may be used in accordance with aspects of the present disclosure. The depicted digital microscopy system 10 includes an objective lens 12, an image sensor 16, a controller 20, a laser autofocuser 44, and a scanning stage 22. In the depicted example, a sample plate 24 is positioned on the scanning stage 22. In certain embodiments, the digital microscopy system 10 may be part of an automated sample plate scanning system and may include a mechanism capable of moving sample plates 24 in an automated manner with respect to the field of view of the scanning optics. In certain embodiments, the sample disposed in the sample plate 24 (e.g., in wells of the sample plate) may be a food or drug sample to be tested for micro-organisms, i.e., either for the absence or the amount of such micro-organisms in the sample.

In practice, the objective lens 12 is separated from the sample plate 24 along an optical axis in the Z (vertical) direction and has a focal plane in the X-Y plane coplanar with the sample plate 24. The objective lens 12 collects light 30 transmitted or reflected by the samples within the sample plate 24 at a particular field of view and directs the light 30 to an image sensor 16. As used herein, the term "light" encompasses any specified wavelength or range of wavelengths (i.e., spectrum) of interest for an imaging operation, whether visible to the human eye or otherwise. In one embodiment, the image sensor 16 generates one or more images of the sample corresponding to a respective field of view at the time the image is acquired based on a primary light path 32. By way of example, a single well or multiple wells of the sample plate 24 containing a sample may be imaged in a single acquisition operation. In certain embodiments, the image sensor 16 may be any suitable digital imaging device, such as a commercially available charge-coupled device (CCD) based image sensor.

The objective lens 12 employed in the digital microscopy system 10 may vary in magnification power based on considerations such as the application and the features to be imaged. In one embodiment the objective lens 12 may be a high power objective lens having a suitable numerical aperture. In one embodiment the objective lens 12 may be spaced from the sample plate 24 in the Z-direction by a suitable imaging distance for the respective application and may collect light 30 from a field of view in a respective focal plane. As will be appreciated, depending on the application, the working distance, the field of view, and the focal plane may vary depending upon the configuration of the digital microscopy system 10 and/or the characteristics of the sample to be imaged. Further, as discussed herein, in embodiments where aspects of the imaging process are automated, such as to allow sequential acquisition of multiple images with respect to a sample plate 24, the digital microscopy system 10 may include a position controller 14, such as a piezo actuator, to provide fine motor control and rapid small field of view adjustment to the objective 12 and/or to adjust the position of the sample plate 24 or a stage 22 on which the sample plate 24 is positioned.

Depending on the imaging protocol or application, the digital microscopy system 10 may illuminate the sample using one or more of a wide variety of imaging modes, including bright field, phase contrast, differential interference contrast, and/or fluorescence. Thus, the light 30 may be transmitted or reflected from the sample in bright field, phase contrast or differential interference contrast applications, or the light 30 may be emitted from the sample in (fluorescently labeled or intrinsic) fluorescence imaging applications. Further, the light 30 may be provided using trans-illumination (where a light source and the objective lens 12 are on opposite sides of the sample) or epi-illumination (where a light source and the objective lens 12 are on the same side of the sample). Therefore, as will be appreciated, the digital microscopy system 10 may include a light source (such as a high intensity LED or a mercury or xenon arc or metal halide lamp) in certain embodiments.

As noted above, in one embodiment the digital microscopy system 10 may be configured as a high-speed imaging system. Such a high-speed system may be configured to rapidly capture a large number of digital images at different spatial locations (e.g., wells) on the sample plate 24. In certain applications, the particular field of view associated with an image may be representative of only a limited fraction of the entire sample plate 24, such as of a well or subset of wells of the sample plate 24. In an example of such an embodiment, the sample plate 24 is imaged repeatedly in adjacent or overlapping areas or is passed in a scanning sweep through the image acquisition area, i.e., field of view. In one such embodiment, an image is acquired, the stage 22 is advanced in the X and Y direction to a position in which an adjacent or overlapping area is moved into the field of view, and another image is acquired. Alternatively, in other implementations, a large number or all wells of a respective sample plate may be measured at once such that only one or a limited number of images is acquired for a given measurement cycle.

As depicted in the present embodiment, the digital microscopy system 10 may also include a processing subsystem 36 that may facilitate the execution of an automated imaging protocol and/or the processing of image data acquired by the digital microscopy system 10. For example, the processing subsystem 36 may be configured to generate or analyze an image generated from acquired optical data. The processing subsystem 36 may also communicate with a display device (i.e., a screen or monitor) to cause the display of the acquired images or a composite or modified image (e.g., a false color image) generated using the acquired image data. Although the memory 38 is shown as being separate from the processing subsystem 36 in the depicted example, in certain embodiments the processing subsystem 36 and memory 38 may be provided together, i.e., as a single or coextensive component. Additionally, although the present example depicts the processing subsystem 36 as being a separate component from the controller 20, in other embodiments, the processing subsystem 36 may be combined with the controller 20 or may function as the controller 20.

As noted above, the digital microscopy system 10 in the depicted example also includes a laser autofocuser 44, which may be used during operation to facilitate image acquisition as well as to perform calibration or normalization operations. As part of its operation, the laser autofocuser 44 may emit infrared (IR) light (or other suitable wavelengths) in the form of a coherent laser beam toward the sample plate 24 and collects back reflected signal to generate focus information or information conveying the depth or amount of sample in wells of the sample plate 24. As the laser spot is scanned through a sample within a sample well, the amount of back reflected light varies with the change of index of refraction seen by the laser spot at its focus position. Back reflected light is then collected via a photo-detector and recorded as a function of Z position. This data may be used as discussed herein to assess the amount of sample within a given well of the sample plate 24, such as by locating a respective air/liquid interface indicate of a fill line or height within a respective well.

Figure 2:
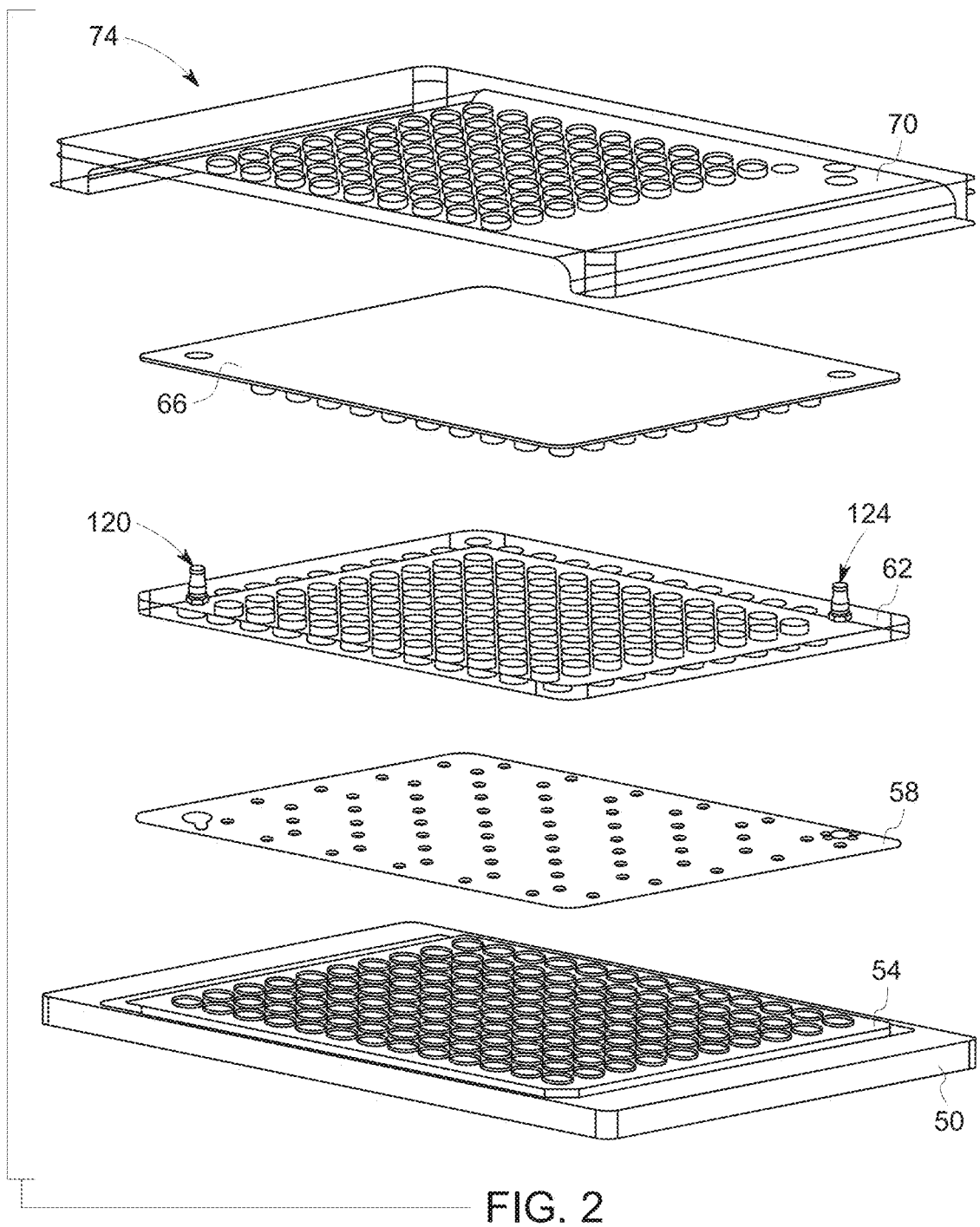
FIG. 2 illustrates an exploded view of layers of one implementation of a sample partition device, in accordance with aspects of the present disclosure.

With the foregoing in mind, FIG. 2 depicts an exploded view depicting "layers" and other features of one embodiment of a sample plate 24 that is configured as a sample partition device 74 in accordance with aspects of the present disclosure. The use of the terms "layer" or "plate" as used herein is intended to encompass one or both of structural of functional aspects of the sample partition device 74 and is used primarily to simplify discussion of various aspects of the sample partition device 74. It should be appreciated, however, that in practice the features or structures discussed herein as discrete layers or plates (in order to streamline and simplify discussion) may be combined into a single structural piece and/or may have the functionality discussed herein as being attributable to multiple or different layers or plates effectively combined into single or combined manufactured pieces for production purposes. For example, pieces or components of the sample partition device 74 may be manufactured using suitable processes (e.g., three-dimensional molding, additive manufacture, unitary manufacture, heat stacking processes or thermal bonding) to provide the functionality of multiple "layers" or plates as described herein into a single piece or component (e.g., an additive manufactures or a molded silicone piece). Conversely, what is described for the purpose of explanation herein as a single "layer" or "plate" may in practice be manufactured as multiple, separate discrete pieces or sheets. Thus, it should be understood that use of the terms "layer(s)" or "plate(s)" herein is to simplify structural and functional features for the purpose of explanation and is not intended to be limiting and/or to preclude constructions or interpretations in which the described structural or functional features are provided on aggregated or separated structures as part of a manufacturing design choice.

With the preceding in mind, in the depicted example the sample partition device 74 includes a well plate or piece 54 (e.g., a well plate, such as a microtiter plate) that includes an array of wells or other chambers into which a sample may be dispensed for testing or incubation. The well plate 54 may be sized so as to fit within a sample plate holder, such as may be present on the scanning stage 22 of the digital microscopy system 10, and may be optically transparent (either the entire well plate 54 or the floor of each well 80) to allow for real-time inspection. Alternatively, the well plate 54 may be positioned or fit within a holder or spacer piece 50 sized and shaped to fit within a sample plate holder of a respective digital microscopy system 10. In certain implementations, the well plate 54 may be manufactured using injection molding techniques and a material that exhibits suitable sterilization possibilities, biocompatibility, and low leaching. One example of such a material is polyethylene, which is gamma sterilizable, exhibits favorable biocompatibility, and has low leachable content.

Figure 3:
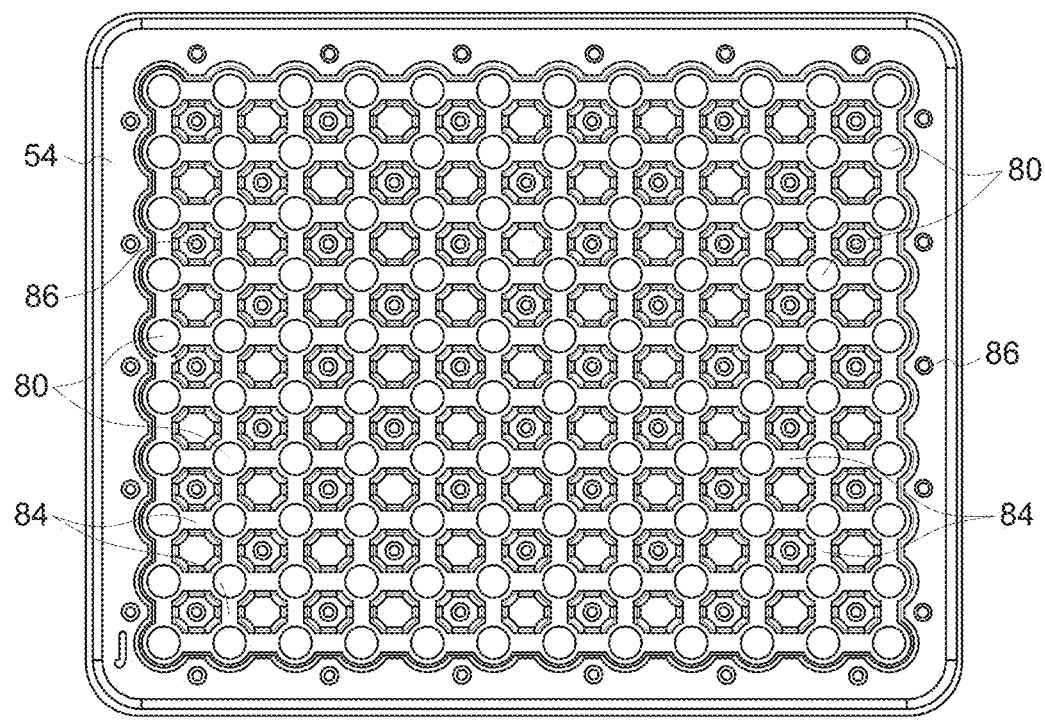
FIG. 3 depicts a plan view of a first embodiment of a well plate, in accordance with aspects of the present disclosure.
Figure 4:
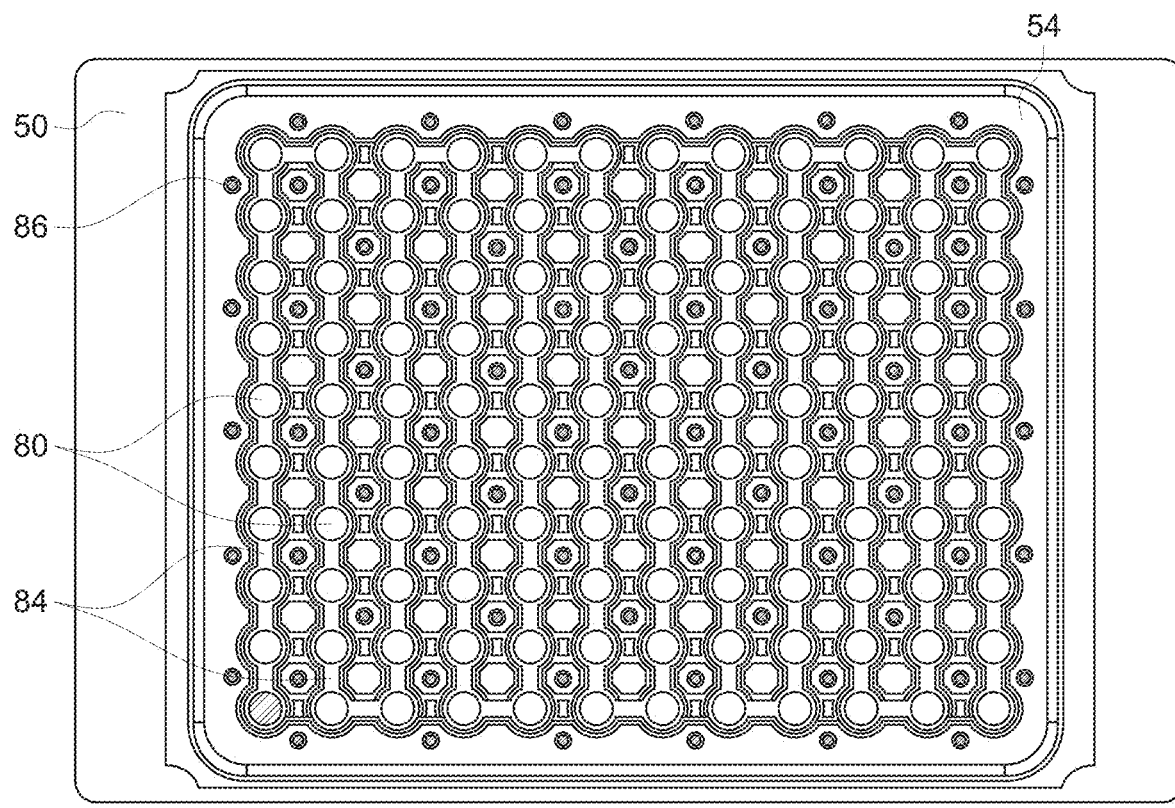
FIG. 4 depicts a plan view of a second embodiment of a well plate, in accordance with aspects of the present disclosure.

Turning to FIGS. 3 and 4, respective plan views are shown of two different configurations of a well plate 54 suitable for use with the present technique. In FIG. 3, a "propagate" design of interconnecting wells 80 is illustrated. In this example, each well 80 is connected to neighboring wells by a mesofluidic channel 84 such that when filled beyond the height of the channel floor, sample fluid in a respective well will flow to a neighboring well. As used herein, a mesofluidic channel 84 should be understood to correspond to millimeter-to centimeter-sized fluid paths (with respect to diameter or cross-section height), the smallest being at least more than 1 millimeter (i.e., not microfluidic) and ranging up to 10 centimeters. Filling of the well plate 54, as discussed in greater detail herein, is accomplished by introducing the sample fluid via an entry port (discussed as part of another layer below) to a respective well or wells 80 and allowing the sample fluid to equilibrate between wells 80 by flowing through the channels 84. In addition, the well plate 54 is illustrated as including a plurality of alignment or mating features 86 that may interface with complementary features of some of all of the other layers discussed herein.

Turning to FIG. 4, an alternative embodiment is illustrated in which each well 80 is not fluidically coupled to each adjacent neighboring well 80, but is instead only fluidically coupled to two adjacent wells 80 by such channels 84 (or to one adjacent well 80 in the case of the wells at the respective beginning and end of the flow path formed by the fluidically linked wells). In this manner, a single flow path of linked wells 80 is created corresponding to a "serpentine" design in which sample, when applied, fills the wells 80 in a defined sequence based on the limited and defined channel connections between wells 80. That is, in such an arrangement each well 80 is fluidically connected so as to form a single fluid path such that the wells 80 along the path are filled one by one as sample is loaded. Filling of the well plate 54 may be accomplished by introducing the sample fluid via an entry port to a respective well 80 (e.g., a first well in the path) and allowing the sample fluid to equilibrate between wells 80 by flowing through the channels 84 as sample is added. Air may be pushed (such as through the use of a sterile syringe) through the entry port to clear the connecting channels of sample so that all of the fluid sample is in a well 80. In addition, the well plate 54 is illustrated as including a plurality of alignment or mating features 86 that may interface with complementary features of some of all of the other layers discussed herein.

Figure 5:
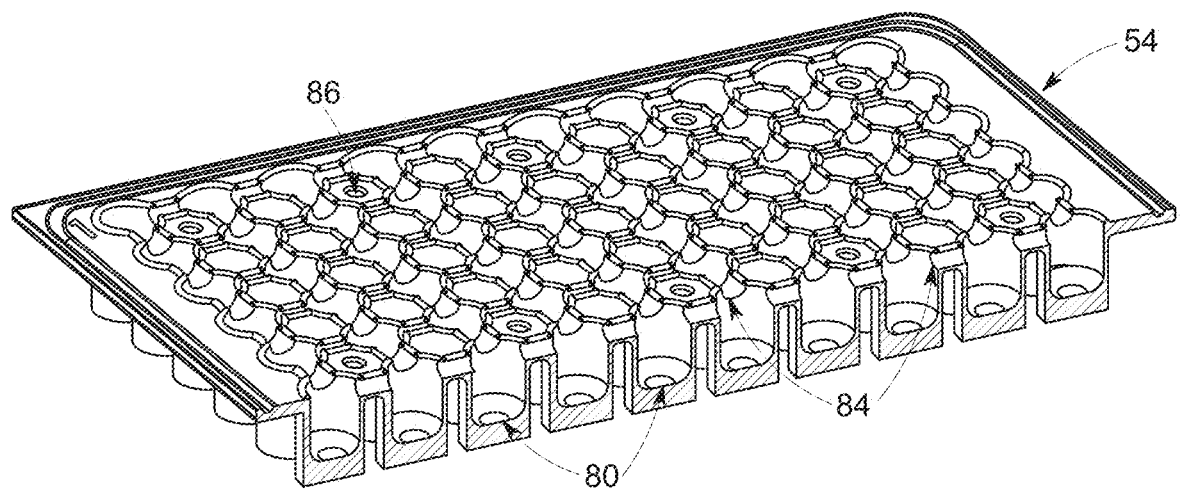
FIG. 5 depicts a perspective cut-away view of an implementation of a well plate, in accordance with aspects of the present disclosure.
Figure 6:
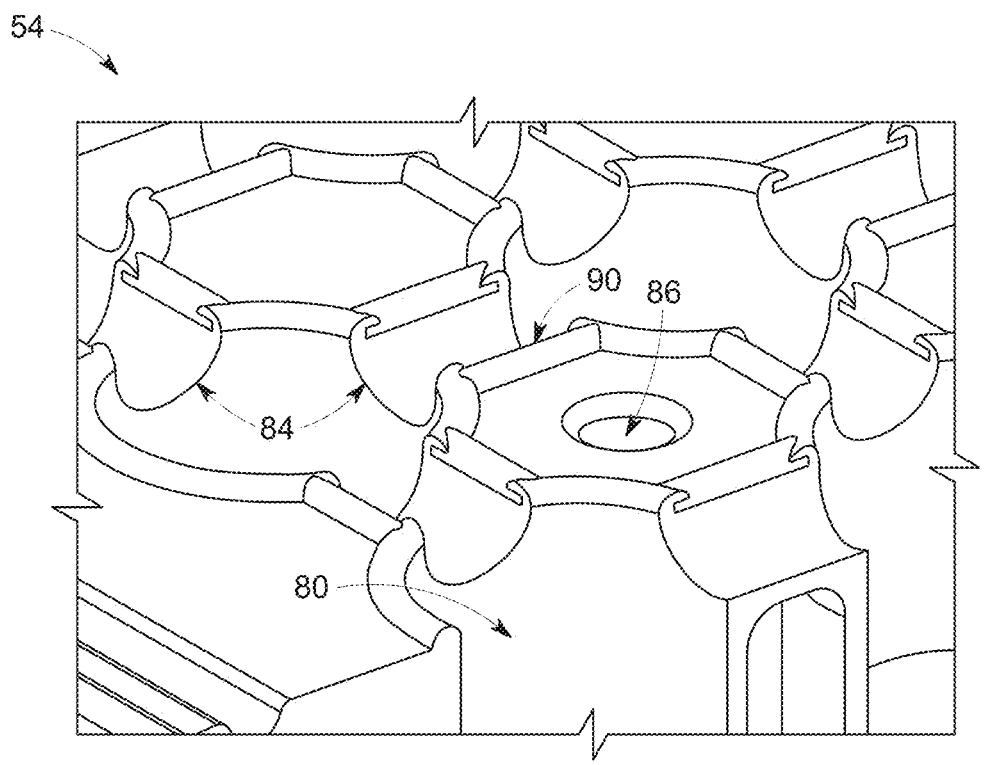
FIG. 6 depicts a close-up of features of a well plate as shown in FIG. 5, in accordance with aspects of the present disclosure.

Turning to FIGS. 5 and 6, a cut-away perspective view of one embodiment of a well plate 54 is illustrated, with FIG. 6 illustrating a close-up view of certain features. In these figures, wells 80 are shown in which a sample may be disposed, such as to allow growth of micro-organisms present in the sample over time. Channels 84 or other structures or features through which the fluid sample may flow connect each well 80 to some of all of the neighboring wells 80. An alignment or mating feature 86 (here depicted as a stud hole sized to receive a stud provided on another layer of the sample partition device 74) is also provided at various locations on the well plate 54. Further, as shown in FIG. 6, in certain embodiments a raised bumper or ridge 90 may be provided to help retain fluid sample within the fluidically connected space defined by the wells 80 and channels 84.

Returning to FIG. 2, a compliant layer 58 is provided over the well plate 54 in the assembled sample partition device 74. The compliant layer 58 thereby helps seal the well plate 54 from the environment by covering the wells 80 so as to preserve a sterile environment. When positioned over the well plate 54 and mesofluidic channels 84, in some embodiments the compliant layer 58 creates a transient manifold to assist in directing a sample fluid into each well 80. The compliant layer 58 may interact or interface with the mesofluidic channels 84 so as to create an enclosed flow path or regulate flow.

In one embodiment the compliant layer 58 is a silicone membrane layer that, in one implementation, may be between 50 μm and 500 μm (for example, 200 μm) in thickness. More generally, the compliant layer 58 is of a composition and thickness so as to be deformable in response to applied pressure or force, such as applied by an overlying layer or plate, and may thus be manipulated by the use of applied pressure to help seal each well 80 and/or mesofluidic channel 84 from the others when in use (i.e., after the sample partition device 74 has been loaded). In some embodiments, the compliant layer 58 may additionally serve to regulate gas exchange (i.e. permit or block oxygen permeability).

Figure 7:
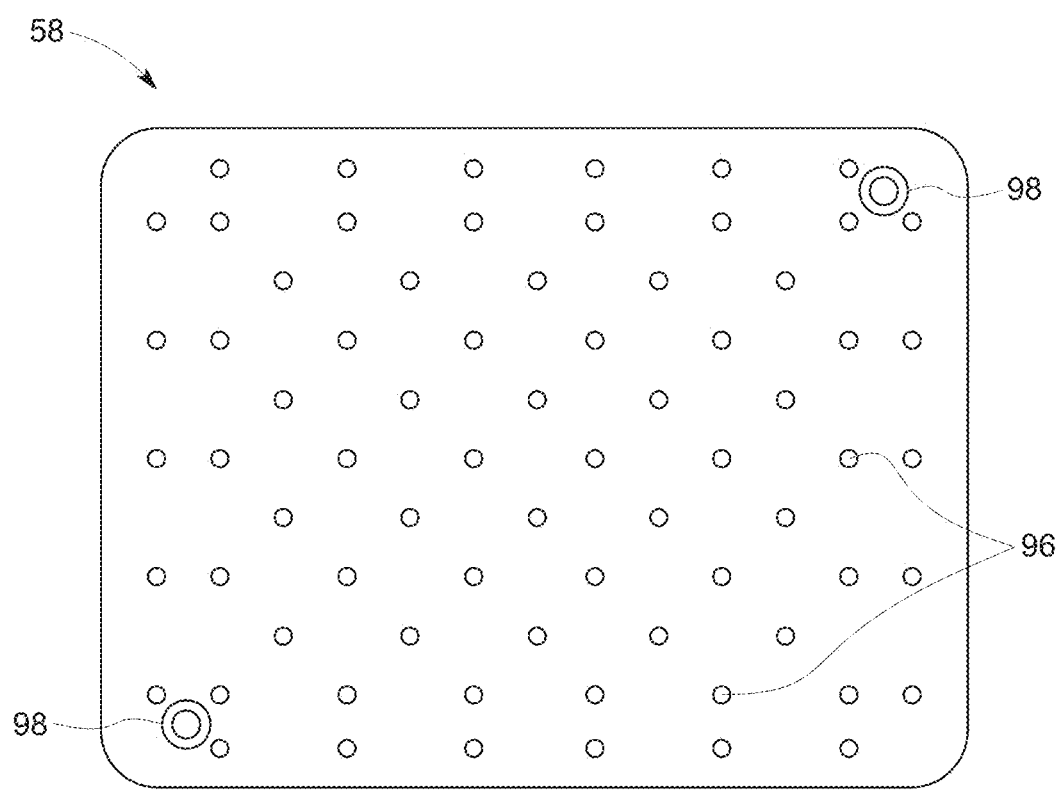
FIG. 7 depicts a plan view of an implementation of a compliant layer, in accordance with aspects of the present disclosure.

Turning to FIG. 7, a plan view of one embodiment of a compliant layer 58 is depicted. In this example, the compliant layer 58 is further illustrated as including alignment features 96 that correspond to the alignment features 86 present on the well plate 54. In this manner, an alignment feature on another layer (e.g., an alignment stud) may pass through the compliant layer 58 to engage with complementary features on the well plate 54 or vice versa. In addition, in the embodiment shown in FIG. 7, circular sealing elements 98 are also provided on the compliant layer 58 coinciding with the location of the inlet and outlet locations used in filling the sample partition device 74 when assembled. Such sealing elements 98 may help preserve or enhance the sealing functionality provided by the compliant layer 58.

Figure 8:
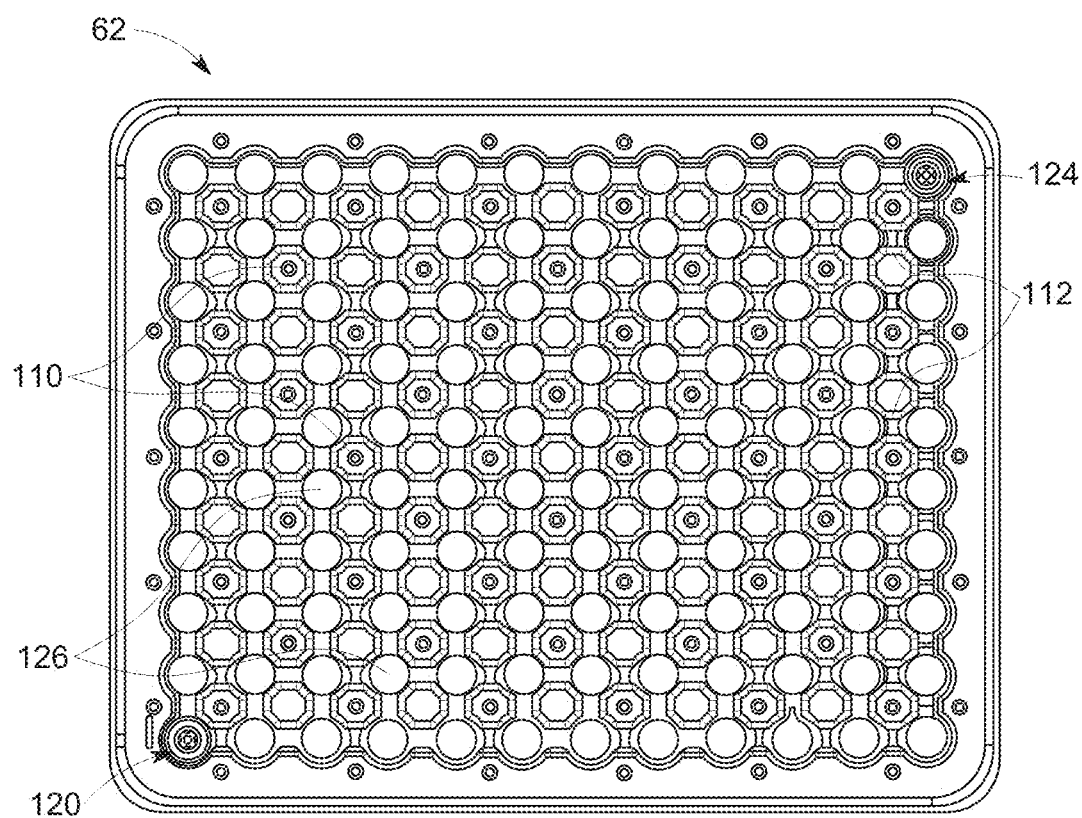
FIG. 8 depicts a plan view of an implementation of a cover plate, in accordance with aspects of the present disclosure.

Returning to FIG. 2, the compliant layer 58 is secured to the well plate 54 using a cover plate 62, a plan view of which is shown in FIG. 8. The cover plate 62, when engaged, acts to mechanically secure the compliant layer 58 and well plate 54 such that the combination of the cover plate 62, compliant layer 58 and well plate 54 (or structural pieces or components providing the described functionality) provide a closed, sterile environment. With this in mind, in practice the cover plate 62, compliant layer 58, and well plate 54 may be pre-assembled in a sterile state and provided to a user in an assembled and ready-to-use state for filling the device. In such circumstances, the assembled combination of these features provides a sterile sample growth environment that is sealed from the outside environment and that can therefore be loaded with the sample by a user in either a sterile or non-sterile environment. Alternatively, a user may assemble the cover plate 62, compliant layer 58, and well plate 54 in a sterile environment for use in a sterile or non-sterile environment.

In the depicted example, the cover plate 62 has a stud and ridge design in which the studs 110 and ridges 112 correspond to complementary features present on the well plate 54 and compliant layer 58. For example, studs 110 of the cover plate 62 may pass through alignment features 96 of the compliant layer 58 to engage with alignment features 86 (e.g., stud holes) present on the well plate 54. Similarly, ridges 112 of the cover plate 62 may correspond to related features (e.g. ridges 90) of the well plate to help maintain a fluid sample within the defined wells 80 and channels 84 of the sample partition device 74. In the depicted example, the cover plate 62 further includes the inlet structure 120 (through which sample may be introduced to the assembled sample partition device 74) and outlet structure 124 (through which air may be released during the fill process).

As noted above, the discrete description and discussion of the functionality provided by the compliant layer 58 and cover plate 62 herein is to simplify explanation by allowing the various functionalities of these layer to be addressed separately. While in practice separate and discrete compliant layers 58 and cover plates 62 may be employed as part of an assembly, it is also possible to combine these functions into a unitary piece or component (e.g., a single piece performing the function attributed to the cover plate 62 and compliant layer 58 as described herein). Indeed, the functionality of the well plate 54 may also be combined in such a single component or piece such a single fabricated, manufactured, or assembled component provides the functionality of each of the well plate 54, compliant layer 58, and cover plate 62 as discussed herein.

Figure 9:
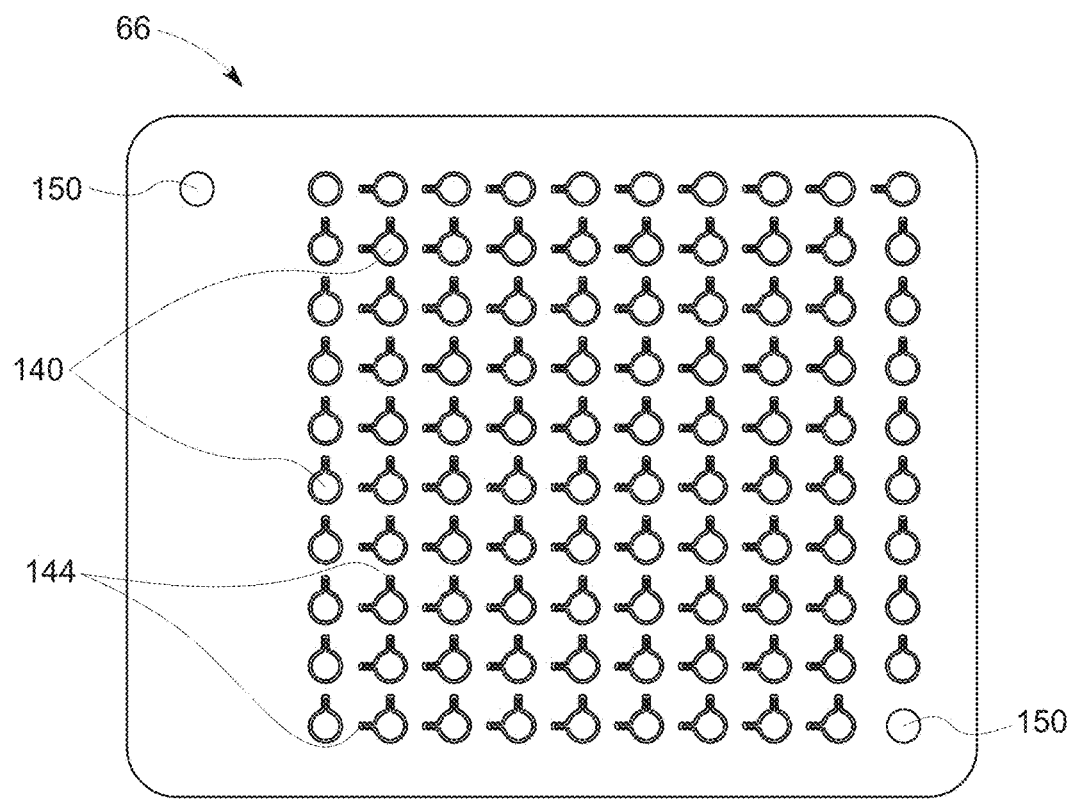
FIG. 9 depicts a plan view of an implementation of an engagement layer, in accordance with aspects of the present disclosure.

In some embodiments, an engagement layer 66 may be applied above the cover plate 62, as shown in FIG. 2. FIG. 9 depicts a plan view of one embodiment of such an engagement layer 66. In the depicted embodiment, the engagement layer 66 includes openings 150 for the respective inlet structure 120 and outlet structure 124 of the cover plate 62.

In the example shown in FIG. 9 the engagement layer 66 has geometric protruding structures (e.g., protrusions 140 corresponding to the well openings and protrusions 144 corresponding to the flow channels). Some or all of these protrusions 140, 144 may be sized and shaped to pass through openings 126 in the cover plate 62 and to engage and deform the compliant layer 58 when pressure is applied. Thus, by pressing the engagement layer 66 toward the well plate 54, pressure is applied to the compliant layer 58 by the protruding structures. In this manner, the protruding structures of the engagement layer 66, when in use or otherwise engaged, act to push sample into each well 80 and to clear any sample present in the channels 84 out of the channels and into a respective well. In addition or in the alternative, forced air may be applied (such as using a sterile syringe) so as to flow under the compliant layer 58 (such as via inlet structure 120) to help remove any remaining sample from the channels 84 and into respective wells 80. In addition to this sample clearing function, when the engagement layer 66 is pushed down and remains engaged, the protruding structures continue to apply pressure to the compliant layer 58 so as to form a seal at each well 80 and keep the sample within the wells 80.

Returning to FIG. 2, the final depicted layer is a secure plate 70 that may be applied once the sample partition device 74 is filled with a sample and the wells 80 are to be sealed one from another. That is, the secure plate 70, when present and secured, acts to apply continued pressure to all or part of the engagement layer 66 so as to thereby press down on the respective portions of the compliant layer 58 to ensure sterility and maintain a seal on each well 80 of the well plate 54.

Figure 10:
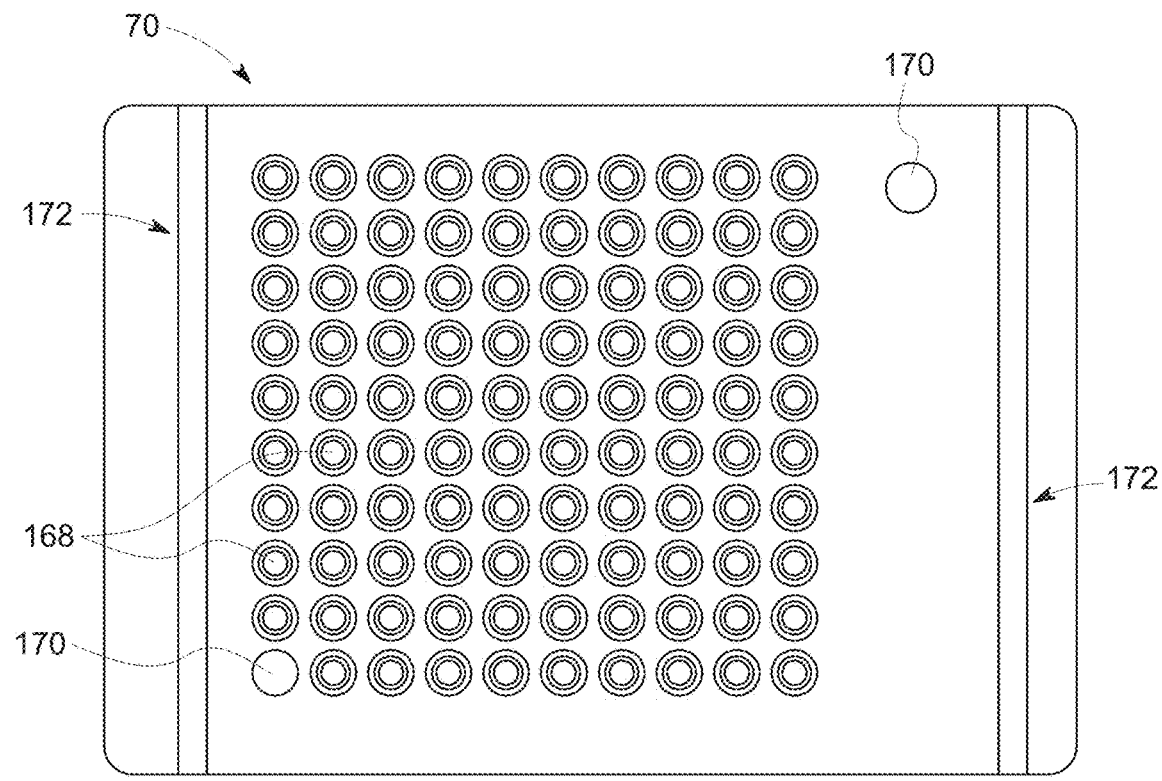
FIG. 10 depicts a plan view of an implementation of a secure plate, in accordance with aspects of the present disclosure.

Turning to FIG. 10, a plan view of one embodiment of a secure plate 70 is shown. In this example, the secure plate 70 includes opening 170 for the respective inlet structure 120 and outlet structure 124 of the cover plate 62 as well as an engagement structure 172 for engaging with a surface (e.g., a bottom surface) of another layer of the sample partition device 74, such as a bottom surface of the well plate 54, when assembled. In this manner, the secure plate 70 may be used to hold all layers of the assembled sample partition device 74 together when in use to allow better handling and optical analysis of the sample partition device 74. Further after filling and sealing, the sample partition device 74 is functionally closed and can be processed in an open and/or uncontrolled environment, i.e., outside of a clean room or other sterile environment.

In the depicted example, the secure plate 70 includes protrusion 168 that correspond to the locations of the protruding structures of the engagement layer 66 the secure plate 70 is engaged. These protrusions 168 help perform the function, described above, of applying continued pressure to the protruding structures of the engagement layer 66 and thereby maintaining a seal on each well 80 once filled with sample and ready for use.

Figure 11:
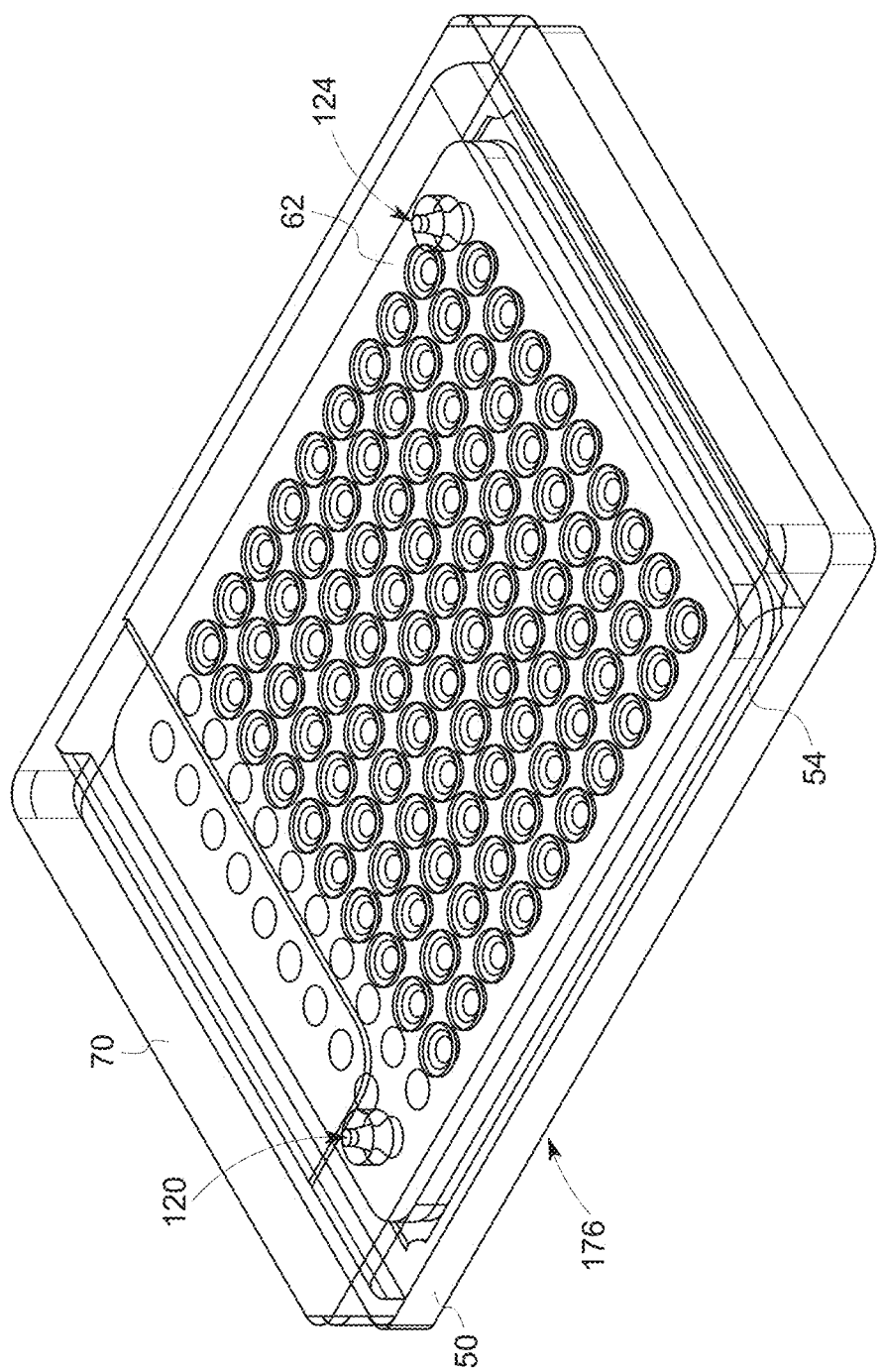
FIG. 11 depicts a unitary structure incorporating the functionality of a well plate, compliant layer, and cover plate into a single structure, in accordance with aspects of the present disclosure.

As noted herein, certain aspects or features described separately above may be combined in practice into a single or unitary piece (i.e., a unitary sample partition device 176). For example, turning to FIG. 11, a single sample partition structure 176 is illustrated that within a single piece or construct incorporates the functionality of providing incubation wells or chambers, a sealing mechanism for sealing such wells or chambers, and a securing mechanism by which the sealing mechanism may be actuated between sealed and unsealed states, (e.g., incorporating the functionality of the well plate 54 (and spacer 50 where appropriate), compliant layer 58, and cover plate 62 into a single structure). This unitary structure 176 may be fabricated or assembled as a single piece and provided for use in this manner (i.e., packaged and shipped as a single piece). In the depicted example, the interconnection of the secure plate 70 to the unitary sample partition device 176 is shown.

With the preceding in mind, in one implementation a portion of the sample partition device 74 (or unitary sample partition device 176 where appropriate) including the well plate 54, compliant layer 58, and cover plate 62 may be filled with a liquid sample (e.g., a sample of an ingestible, inhalable, or injectable drug, a topical or ocular drug, a water or other liquid sample (e.g., a beverage), a liquid sample in which particulates of a material to be tested, such as a pharmaceutical or food substance, are suspended, and so forth) such that all of the sample is partitioned into respective wells 80, with no portion of the sample being untested or wasted. The combination of the well plate 54, compliant layer 58, and cover plate 62 form an environmentally sealed assembly, with only ingress or egress with respect to the wells 80 being via the respective inlet structure 120 and outlet structure 124 of the cover plate 62. After the sample is introduced into and partitioned by this environmentally sealed assembly, an engagement layer 66 (or functional equivalent) may be employed to apply downward pressure on the compliant layer 58, to seal the wells 80 of the well plate 54. As part of or prior to such an operation, the channels 84 may be cleared of sample fluid, either by the application of sterile air under pressure vie the inlet structure 120 or by protruding structures of the engagement layer 66 corresponding to the locations of the channels 84. A secure plate 70 may be added at this point to help secure the assembly together and/or to maintain pressure on the compliant layer 58 to maintain the seal on the wells 80.

The sample-filled wells 80 of the well plate 54 may then be processed over a suitable time interval (e.g., 24-48 hours), with periodic measurements obtained using a suitable measurement system, such as a digital microscopy system 10. In practice, temperature may be leveraged to further accelerate time-to-detection by speeding microbial growth, such as by raising the culture incubation temperature from 22.5C to 32.5C. In addition, depending on the micro-organisms of interest, in certain implementations the sample partition device and/or methodology described herein may be employed in the absence of oxygen to permit assessment of anaerobic growth. In this manner, real-time monitoring of each measurement well 80 may be performed (such as via fluorescent and bright field microscopy), based on the knowledge that measuring x number of distinct wells 80 simultaneously (e.g., 100 wells) is equivalent to measuring the total sample volume.

For example, in one implementation a 10 mL sample of a pharmaceutical may be introduced into a portion of a sample partition device (e.g., an assembly of the well plate 54, compliant layer 58, and cover plate 62 or a unitary structure combining all or some of the corresponding functionality of these layers) through an inlet structure 120 via syringe or gravity feed. Pressurized air may be subsequently applied to ensure that the entirety of the sample is flushed from any inlet tubing and/or valve so as to allow all sample to be tested. In this example, each well 80 may be capable of holding a volume of approximately 0.1 mL before liquid sample flows via channels 84 to a neighboring well 80. Thus, the 10 mL sample may be automatically partitioned between approximately one hundred wells 84 via the action of the sample flowing through channels 84 to neighboring wells 80. Each well may then be monitored for growth of micro-organisms separately via optical techniques (e.g., using a digital microscopy system 10) such that the aggregate of sample within the wells 80 corresponds to the total sample volume. Because the presence of microbial growth is being monitored in a smaller volume than the full sample volume, growth can be detected more rapidly than it would be if only looking for growth in the bulk, un-partitioned sample. By way of example, by assessing for micro-organism growth in smaller, partitioned volumes (i.e., measurement wells), time-to-detection may be accelerated allowing tests to be concluded more rapidly and corrective action to be taken sooner. For example, in one context using the techniques described herein, bacterial growth is detected within 24 hours and yeast and/or mold growth is detected within 48 hours.

To the extent that the volume of sample in wells 80 may vary, in some implementations a laser autofocuser 44 may be employed to determine the fluid level or height of sample within each well 80 (such as by identifying a respective air/liquid interface in each well 80), and thereby the volume of sample in each well 80. For example, a laser autofocuser 44 may be used to determine a fill height for each well 80, and thereby determine the sample volume in each well and, more broadly, whether each well 80 is full, partially full, or empty. Such fill level measurement may be performed periodically in contexts where fill level has the potential to vary over time, such as due to evaporation of the liquid. In this manner, micro-organism growth rates as a function of sample volume may be calibrated or corrected to accurately reflect the actual volume of sample involved. Alternatively, in other embodiments, transmitted light absorbance may be used to determine a fill fraction for each well 80. It may be noted that empty wells may be present when a well plate 54 is employed having a total well volume that is greater than the volume of the sample, i.e., more wells 80 than can be filled with the sample. Such "over-provisioning" of wells 80 assures (taking into account variable and partial filling of wells 80) that all sample can be accommodated in the provided wells 80 so that no sample is lost or not accounted for in the growth analysis.

The ability to read and analyze partially filled wells in this manner may be useful in assuring that the entire sample is processed (i.e., with no sample loss). For example, in practice a greater number of wells 80 may be provided in a given sample partition device 74 than is necessary to accommodate a given sample volume. This may be beneficial to accommodate partial filling of some wells so that all of the sample ends up in a well 80 and that no sample is lost or unprocessed, even if some wells 80 are only partially filled. As noted above, volume assessment using a laser autofocuser 44, if present, may allow for growth rate correction in such partial filling scenarios so that even a partially filled well 80 yields usable data. In this manner, the provision of excess capacity in a given sample partition plate 74 helps ensure that the entire sample is used.

In another aspect, the present technique may be useful for processing non-filterable samples where solids or particulates may be present but which cannot be filtered as they may be necessary as part of the sample to be tested (for example mammalian cells present in a cell-based therapy or blood-derived product). In particular, image-based detection of microbial cell growth is not affected by particulate matter present in non-filterable samples. For example, fluorescent-based monitoring leads to signal-gain deviation from baseline due to cell growth, whereas bright field-based monitoring leads to signal-loss deviation from baseline due to cell growth. Further, in certain aspects, solids or particulates, if present, may settle over time in each respective well 80. A laser autofocuser 44 in such scenarios may also be used to locate the interface between the settled matter and the sample fluid, allowing focal planes to be established above the level of settling for the purpose of obtaining optical data and measurements related to the growth of micro-organisms in the sample.

With the preceding discussion in mind, the presently contemplated sample partition device 74 may be used in conjunction with a digital microscopy system 10, as shown with respect to FIG. 1, to acquire micro-organism (e.g., bacteria, mold, and/or yeast) growth data for a sample over an incubation interval (e.g., 24 hours to 48 hours) for one or both of a sterility or bio-burden analysis. In one example, a digital microscopy system as shown in FIG. 1 may be used to assess each well 80 for the presence or concentration of a micro-organism over time. Such an analysis may include a baseline subtraction step (e.g., with a baseline derived from sample wells containing only growth media without sample or derived from historical baseline reading).

Detection may be performed via one or both of fluorescent or bright field (i.e., transmission) microscopy, and allows for real-time determination of the presence or absence of micro-organisms. In one implementation, detection is performed using a time-series of measurements acquired at successive time intervals (either fixed or variable) with an appropriate imaging metric applied to determine if micro-organisms are present. As described above, the sample partition device 74 partitions the sample input volume into multiple discrete measurement zones with minimal operator involvement, thereby reducing operator- and environment-based false positives.

With respect to analytics and performed on growth data acquired using a digital microscopy system 10 and sample partition device 74 as discussed herein, in one implementation one or both of sterility testing and bio-burden quantitation may be performed simultaneously using presence/absence detection (for sterility testing) and/or "most probable number" (MPN) statistical methods (for bio-burden testing) across the wells 80 of the sample partition device 74 (i.e., across the partitioned sample). That is, in the context of sterility testing, any growth within any well 80 is indicative of the presence of micro-organisms. Conversely, in the context of bio-burden testing, how many wells 80 show growth and the rate of change in observed growth may be indicate of a quantifiable bio-burden with respect to one or more types of micro-organism (e.g., bacteria, yeast, and/or mold). In practice, such testing may be performed by imaging wells 80 of a sample partition device 74 filled with sample at a regular interval (e.g., hourly) to evaluate each well 80 for changes in the measured parameter (e.g., transmitted light, measured fluorescence, and so forth). Any deviation up or down (e.g., +/−) is indicative of micro-organism growth, with the sequence of measurements over time providing additional data with respect to growth rate, initial concentration, and so forth. With this in mind, in certain implementations statistical enumeration using MPN, as well as presence/absence detection, may be reported a regular intervals or in real-time by summarizing results for all measured wells 80. Further, for those wells 80 in which growth is observed, sample may be retrieved, such as after the incubation period or upon first observation of growth, to allow strain identification.

Figure 12:
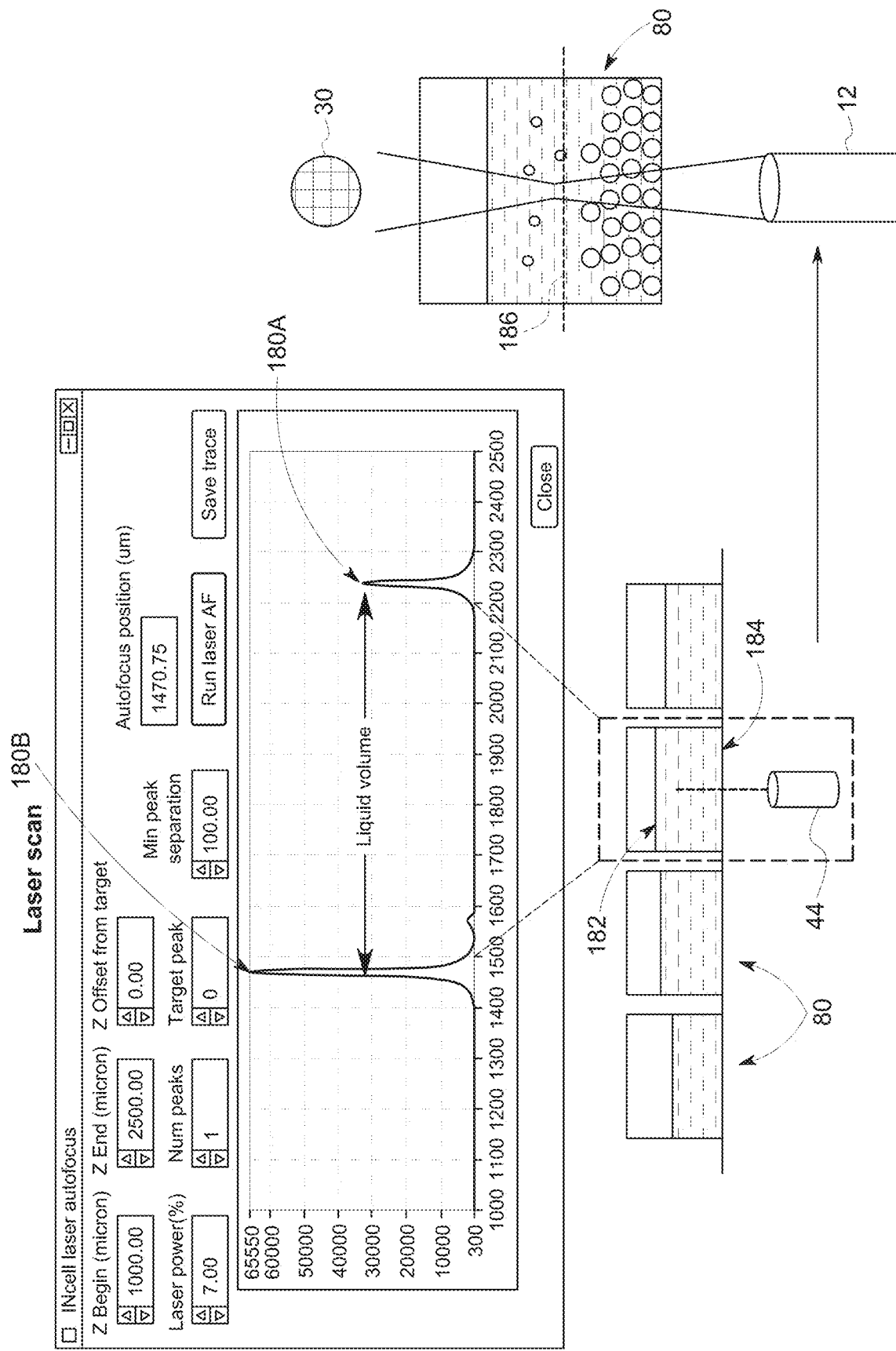
FIG. 12 schematically illustrates use of a laser autofocus component to determine fluid sample height within a well and placement of a focal plane based on the measured fluid sample height, in accordance with aspects of the present disclosure.

In one implementation, a laser-based imaging methodology is employed, such as using a laser autofocuser of a digital microscopy system 10, to accurately characterize the sample volume within each well 80 and to offset the image focal plane 186 within the vertical center of the sample for imaging purposes, e.g., real-time imaging. This is illustrated schematically in FIG. 12 in which a laser autofocuser 44, which may be integrated with or separate from the objective lens 12, may scan through each well 80 to identify peaks 180 corresponding to the relative vertical positions of interfaces between materials with dissimilar indices of refraction, such as the boundary changes at the upper and lower surfaces of the sample. This in conjunction with the known geometry of the wells 80 identifies the upper boundary surface 182 (e.g., the fluid-to-air interface demoting the height of the fluid column, here corresponding to peak 180A) and lower boundary surface 184 (e.g., the air-to-plastic interface denoting the bottom of the well, here corresponding to peak 180B) that may be used to determine the volume of the sample within a respective well 80. Based on the measured sample volume within a respective well, the vertical positioning of the focal plane 186 (here shown with respect to an objective lens 12 illuminated by a light source 30) may be determined, such as to be vertically centered within the sample volume of a well 80 or, depending on particulates that may be present, at a desired or suitable vertical offset relative to any settled particles that are present. Further, because the array geometry of the wells 80 is known, a mass-balance analysis of volume across the array may be used to confirm complete filling and to enable a quality control workflow to verify zero-loss of sample.

Figure 13:
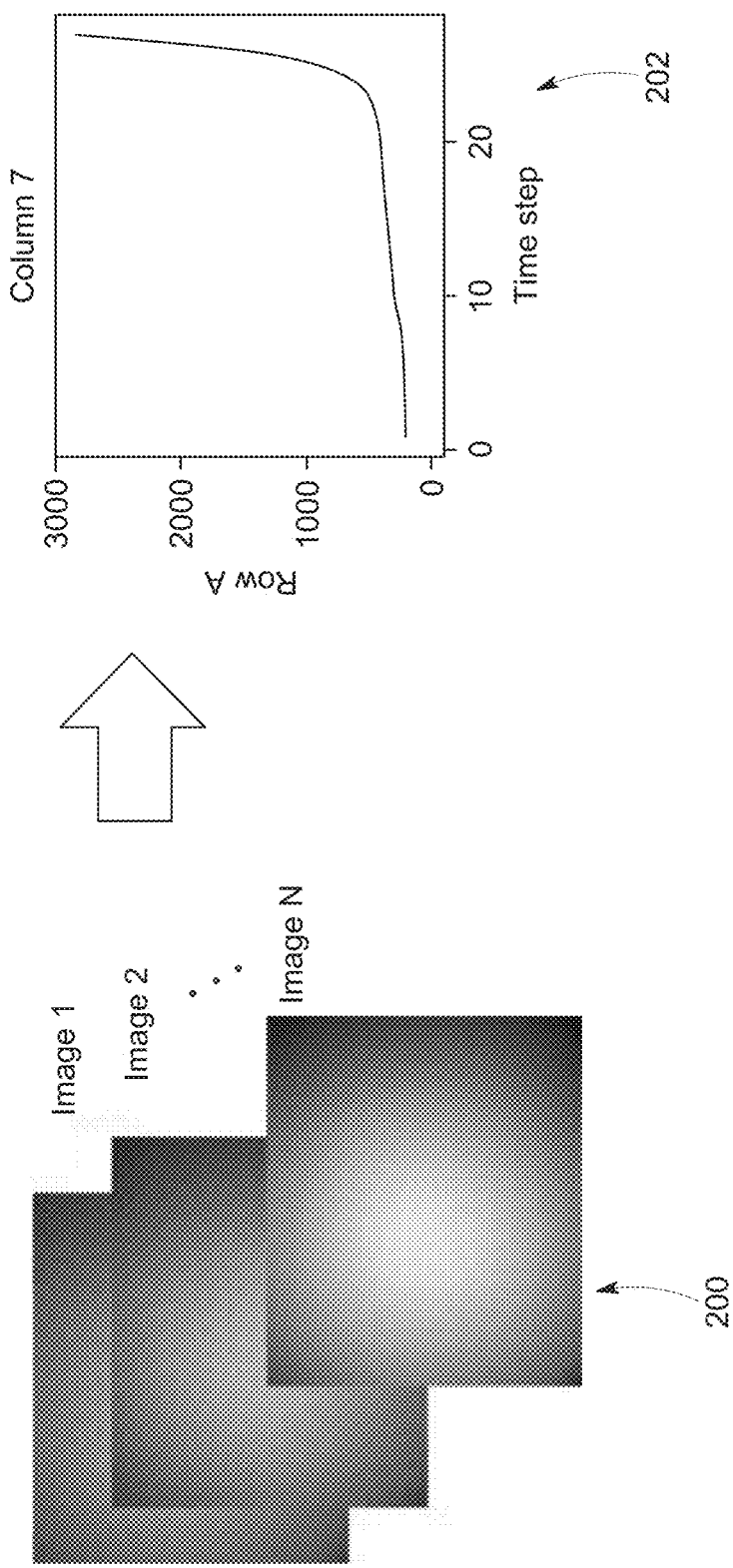
FIG. 13 depicts an example of a series of images acquired of a well over time and a corresponding graph of mean intensity over time, in accordance with aspects of the present disclosure.
Figure 14:
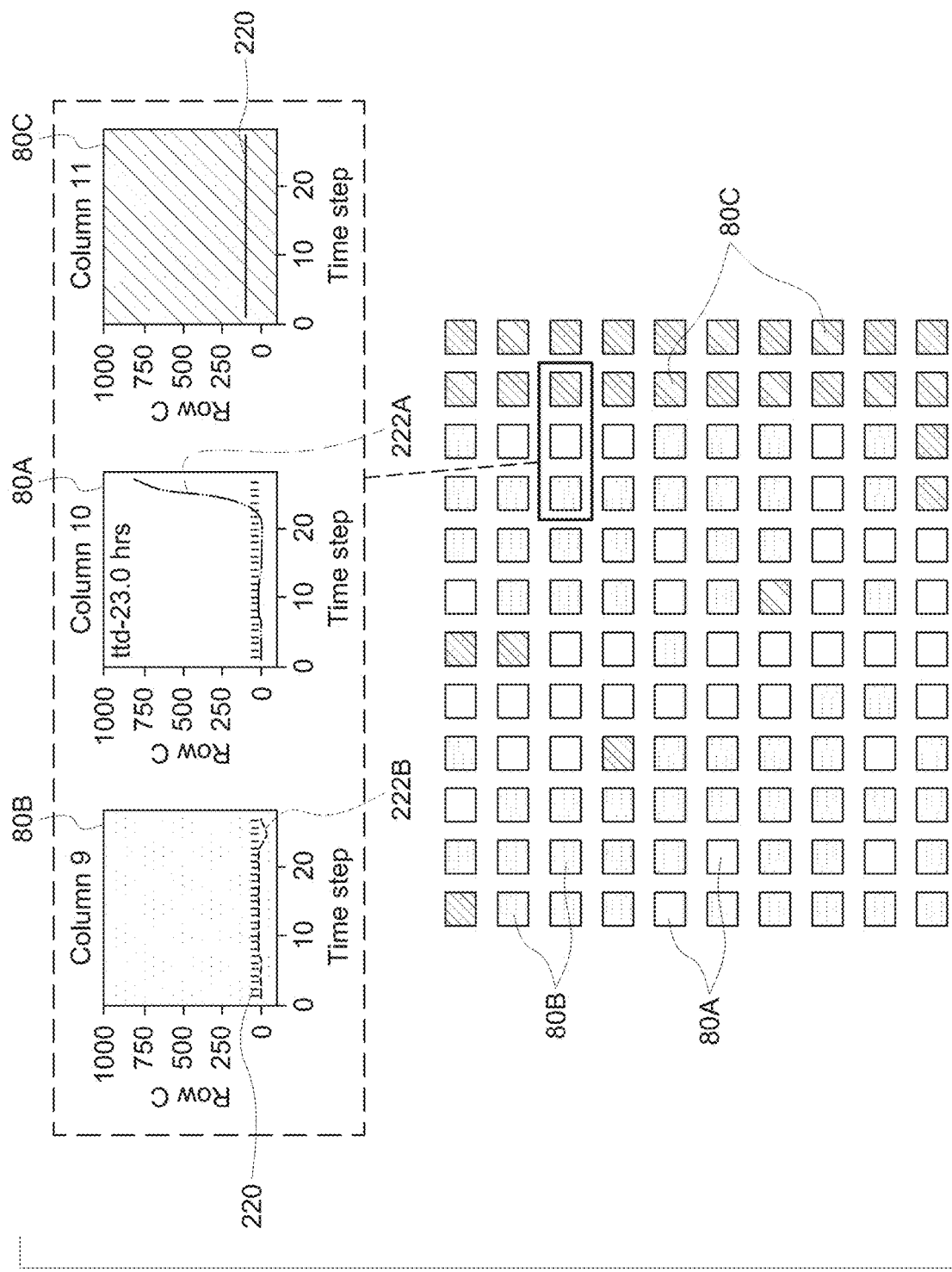
FIG. 14 graphically depicts assessment of wells of a sample partition device for micro-organism growth, in accordance with aspects of the present disclosure.

With the preceding discussion of data acquisition and analytics in mind, FIGS. 13 and 14 illustrate additional examples of measurement and analytics so as to clarify or illustrate the relevant concepts. For example, turning to FIG. 13, a sequence of images 200 are illustrated corresponding to images acquired of a respective sample-filled well 80 (here the well located at row A, column 7 of a respective sample partition device 74) at different times (e.g., hourly intervals). In this example, the sample was a 10 mL sample with images captured of each well 80 hourly. For a 120 well sample partition device 74, such a data acquisition scenario equates to 120 images per time point, which results in approximately 3,000 to 6,000 images per test. The image data (as represented in the images 200) was converted to mean intensity values, which may be plotted over time, as illustrated in the graph 202 where mean intensity is represented on the y-axis and time is represented on the x-axis. In this manner, for each respective well, the change in observed mean (or median) intensity over time may be readily observed.

While FIG. 13 illustrates this concept for a single well 80 over time, FIG. 14 represents this approach for this example in the context of the entire sample partition device 74, with visual indexing (e.g., color coding) employed to facilitate quick interpretation of results. Such color coding may be useful in contexts where each well 80 is classified as positive, negative (for presence of micro-organisms or micro-organisms exceeding a suitable threshold), or empty and, when viewed over time, may be used for determining or may be used to illustrate time-to-detection. By way of example, in the sample shown in FIG. 14 the array of wells 80 of a sample partition device 74 are illustrated and are visually coded to illustrate which wells are empty (80C), which are positive for growth of micro-organisms (80A), and which are negative for growth of micro-organisms (80B).

In the depicted example, a representative well of each type (corresponding to the wells found in row C, columns 9-11) is enlarged and shown. Each representation includes a baseline 220, which may be derived from measurements of growth media only, with no sample, and against which new observations may be compared to assess growth. In practice, the control data used to derive the baseline data may be measured on a separate sample plate, measured on the same sample partition device 74 but in a region isolated from the remainder of the device and having a separate inlet and outlet, or may be derived from historical or empirical observations believed to be representative of a baseline. In the non-empty wells, the graphed mean intensity over time is shown to trend (line 222B) near the baseline 220 for the well 80B deemed to be negative for growth and trends upward and away (line 222A) from the baseline 220 over a suitable incubation period in the well 80A deemed to be positive for growth.

With respect to the detected growth, an example of a methodology for calculating the most probable number (MPN) of organisms contained in the sample partition device 74 is to determine the number of wells determined to be positive for growth relative to all wells containing sample. In the depicted example, 35 well are positive for growth (wells 80A) and 58 wells are negative for growth (80B) (with 27 wells containing no sample). Thus 93 total wells 80 contain sample, of which 35 exhibit growth. In this example, this equates to an estimated most probable concentration of 4.7 CFU/mL.

Turning to FIG. 15, a further analytics example is illustrated in which time-to-detection is emphasized. In this example, real-time bacteria (E. coli, quality control strain #25922) detection in tryptic soy broth was performed using a sample partitioning device 74 as described herein and measuring resazurin by fluorescence. The expected time-to-detection for one E. coli cell per well 80 was approximately 20 hours based on manual testing. The labeling of the grid shown in FIG. 15 indicate "AIR" for wells 80 in which no sample was present and are blank for wells where no growth was detected as a function of deviation from the baseline value. For wells 80 in which growth was detected as a deviation from baseline, a number is shown in the cell corresponding to the respective well 80, in which the number corresponds to the time-to-detection (TTD) in hours. In this example, the average time-to-detection was approximately 21.5 hours, which is within one standard deviation of the expectation.

Figure 16:
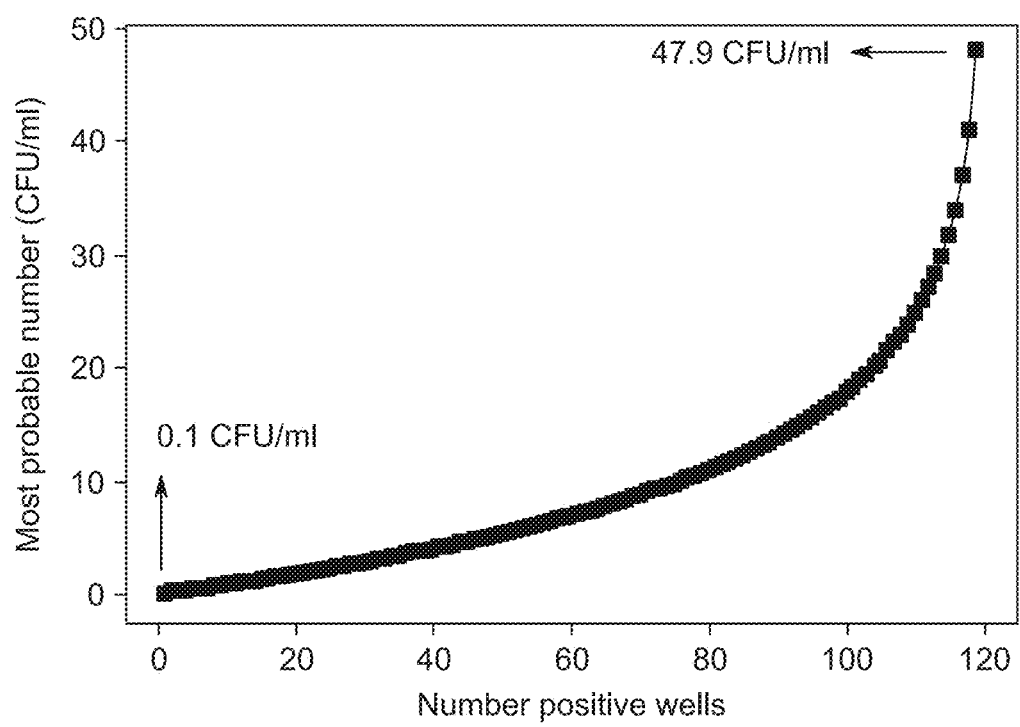
FIG. 16 graphically depicts dynamic range of a sample partition device, in accordance with aspects of the present disclosure.

Turning to FIG. 16, an example calculation is provided demonstrating the dynamic range (i.e., the difference between the largest and the smallest signal values) that may be obtained for a sample partition device 74 (e.g., a 120 well sample partition device) as described herein. In particular, FIG. 16 illustrates a plot of the "Most Probable Number" in terms of CFU/mL) versus the number of positive wells (ranging from 0 to 120 and assuming all 120 wells are filled with sample). In this example, a lower limit and an upper limited may respectively be characterized as:

$$\text{lower limit} = \frac{1}{v}\log\left(\frac{n-1}{n-2}\right) \approx \frac{1}{nv} \quad (1)$$

and $$\text{upper limit} = \ln(n)\frac{1}{v} \quad (2)$$

where n is the number of wells 80 and v is the volume of an individual well. Assuming all wells 80 are filled and such that n=120 and for v=0.1 mL, a lower limit of 0.1 CFU/mL and an upper limit of 47.8 CFU/mL are calculated, as plotted in FIG. 16. In practice, partial filling has little impact on the dynamic range associated with the sample partition device 74 and, if a laser autofocuser or other mechanism is used to determine and adjust for the actual sample volume in each well 80, the partial filling of wells 80 may be fully addressed as calculations for each well may be based on the actual sample volume in each well.

Figure 17:
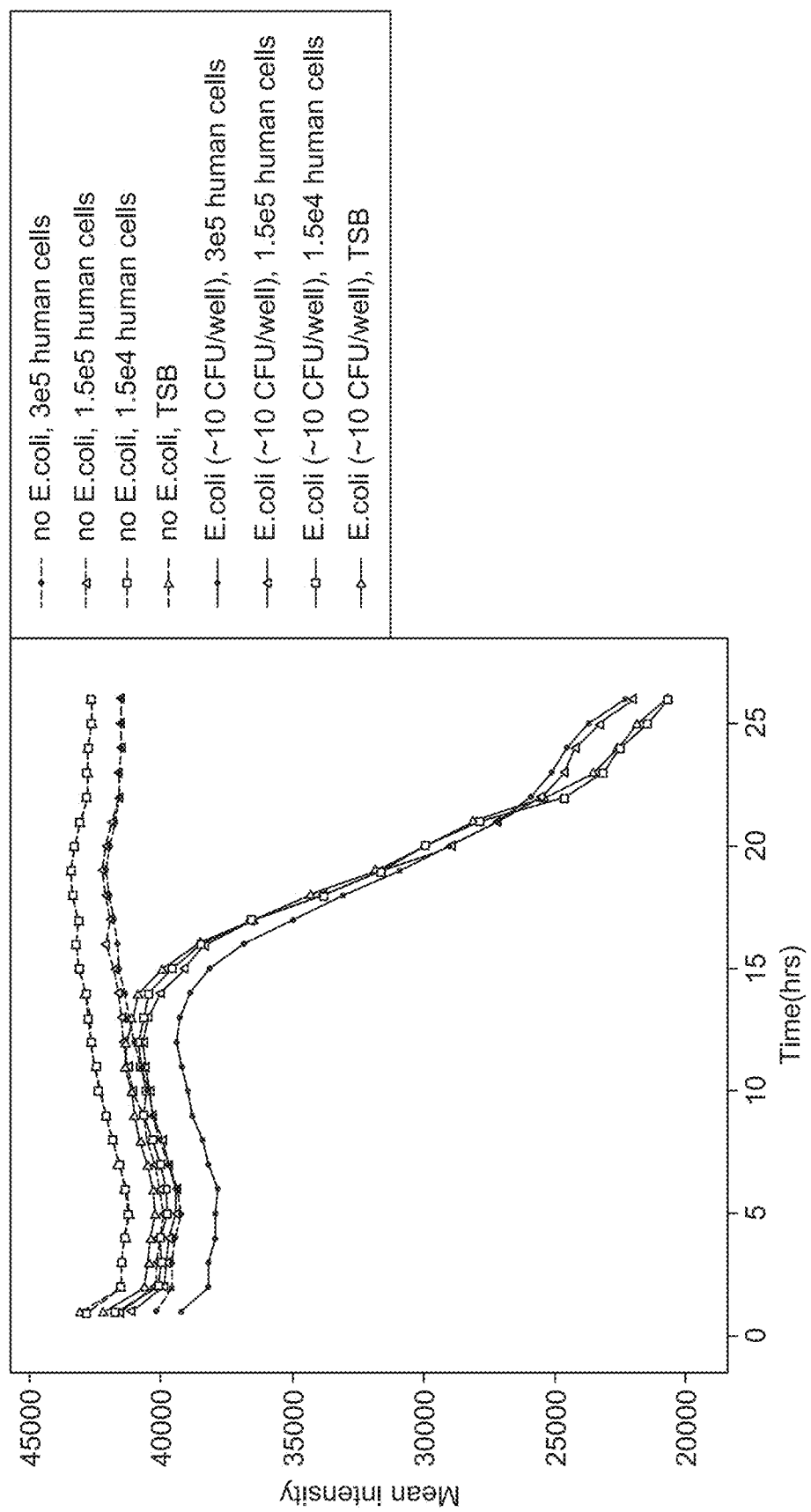
FIG. 17 graphically depicts time-to-detection of *E. coli* in the presence of human cells, in accordance with aspects of the present disclosure.

With the preceding in mind, FIG. 17 illustrates a further set of experimental results. In this example, bright field detection of microbes (E. coli quality control strain #25922) in the presence of human cells was performed in tryptic soy broth, which is consistent with contexts having a non-filterable drug, like cell therapy drugs. Incubation was at room temperature and optical properties (e.g., mean intensity) indicative of E. coli growth were monitored in the presence of human cells. Study conditions and results are set forth in Table 1 as follow:

TABLE 1

| Human Cells/ Well | Bacteria/ Well | Well Volume | Time-to-detection (TTD) (hrs) |
|---|---|---|---|
| 0 | 10 | 110 μL | 16.4 ± 0.92 |
| 2.5 × 10$^5$ | 10 | 110 μL | 16.1 ± 0.99 |
| 1.4 × 10$^5$ | 10 | 110 μL | 16.5 ± 0.71 |
| 1.5 × 10$^4$ | 10 | 110 μL | 17.5 ± 0.71 |

With these experimental conditions in mind, FIG. 17 graphically plots mean intensity for each of these experimental conditions against time, along with corresponding control measurements in the absence of bacteria. As may be seen in Table 1 and FIG. 17, time-to-detection (TTD) using the present techniques was between sixteen and eighteen hours in each experimental scenario.

Figure 18:
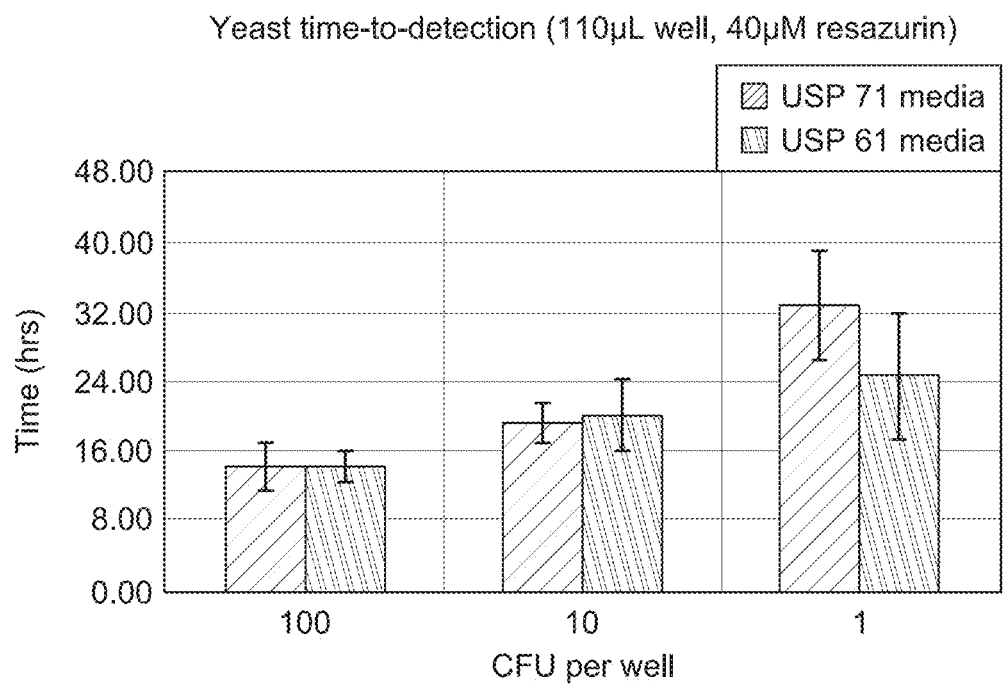
FIG. 18 graphically depicts time-to-detection of yeast growth in wells of a sample partition device, in accordance with aspects of the present disclosure.
Figure 19:
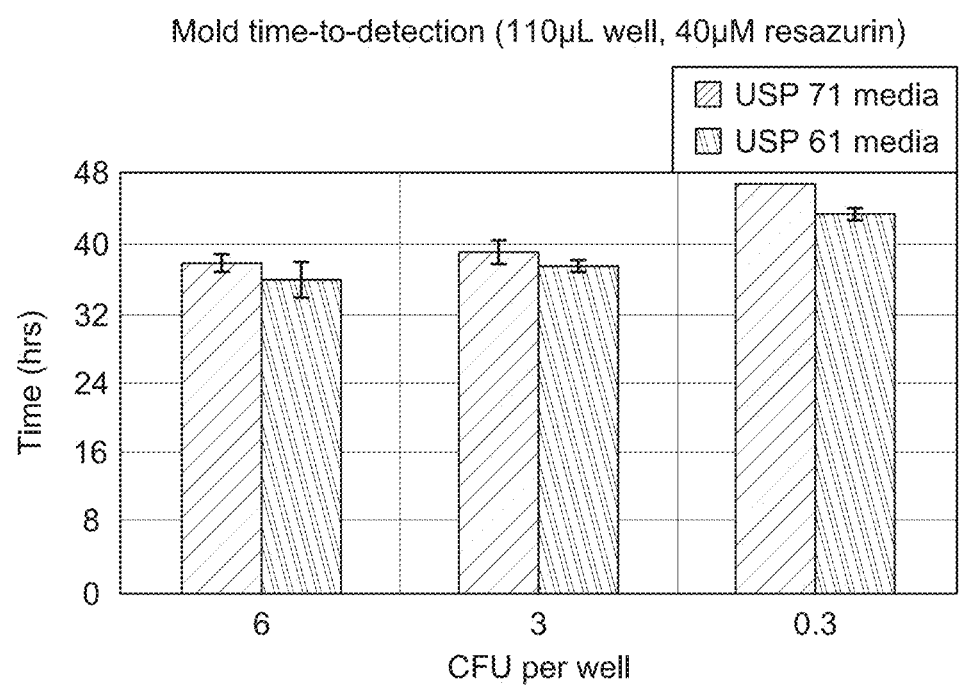
FIG. 19 graphically depicts time-to-detection of mold growth in wells of a sample partition device, in accordance with aspects of the present disclosure.

The preceding examples demonstrate the efficacy of the described techniques in assessing bacterial growth rapidly (e.g., in 24 hours). Turning to FIGS. 18 and 19, the efficacy of the present techniques for rapidly assessing yeast and mold growth is also shown. In particular, FIG. 18 demonstrates yeast time-to-detection in two studies in accordance with the present approach. In each case, time-to-detection of yeast (Candida albicans quality control strain #10231) is less than 40 hours. FIG. 19 similarly demonstrates mold time-to-detection in two studies in accordance with the present approach. In each case, time-to-detection of mold spores (Aspergillus brasdiensis quality control strain #2275) is less than 48 hours.

Technical effects of the invention include an easy to load, sterile, consumable device (i.e., a sample partition device) is provided for use with a microscope imager and integrated analytical software. The sample partition device can be used to test a sample for absence of microorganisms (sterility) and/or for concentration of said organisms (bio-burden). All of the sample may be contained in the sample partition device with zero-loss and the device may be employed with both filterable and non-filterable samples. The sample partition device partitions the sample input volume into multiple discrete measurement zones with little or no loss of sample (e.g., zero-loss) and with little operator involvement, thereby reducing operator- and environment-based false positives.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A cell analysis system, comprising:
   an imaging sub-system configured to automatically acquire successive images; and
   a processing sub-system configured to control operation of the imaging sub-system and to process data acquired using the imaging sub-system, wherein the imaging sub-system and processing sub-system in cooperation perform acts comprising:
      measuring a fill height of each sample-containing well of a plurality of wells of a well plate, wherein the sample-containing wells contain a sample that is partitioned between the sample-containing wells;
      determining a focal plane height for each sample-containing well based at least in part on the respective fill height of sample within each sample-containing well;
      acquiring, using the focal plane height determined for each sample-containing well, successive images of the respective sample-containing wells;
      determining, using the acquired successive images, a change in a measured optical parameter at each sample-containing well over time relative to a baseline; and
      generating an assessment of micro-organism presence within the sample based on the determined changes in the measured optical parameter at each sample-containing well over time.

2. The cell analysis system of claim 1, wherein the imaging sub-system comprise a digital microscopy system.

3. The cell analysis system of claim 1, wherein measuring the fill height of each sample-containing well comprises:
   scanning through each sample-containing well using a laser auto-focuser of the imaging sub-system to generate laser scan plots for each sample-containing well; and
   identifying peaks associated with the changes in indices of refraction indicative of a bottom of the well plate and height of the fluid column within each respective sample-containing well.

4. The cell analysis system of claim 1, comprising:
   determining a volume of sample within each sample-containing well using the respective fill heights.

5. The cell analysis system of claim 4, wherein the volume of sample within each sample-containing well is determined using the fill height for a respective sample containing well and a known geometry of the wells of the well plate.

6. The cell analysis system of claim 5, wherein the assessment of microorganism presence within the sample is based at least in part on the volume of sample within each sample-containing well.

7. The cell analysis system of claim 1, wherein the assessment of micro-organism presence within the single sample comprises one or both of an assessment of sterility or a quantification of bio-burden.

8. The cell analysis system of claim 7, wherein the quantification of bio-burden comprises a most-probable number determination based on a number of sample-containing wells exhibiting micro-organism growth relative to the baseline.

9. The cell analysis system of claim 1, wherein the micro-organism presence comprises bacterial presence, yeast presence, or mold presence, or combinations thereof.

10. A method for assessing microorganism presence within a sample, comprising:
    partitioning a sample between a plurality of wells of a well plate to form a plurality of sample-containing wells;
    measuring a fill height of each sample-containing well of the plurality of sample-containing;
    determining a focal plane height for each sample-containing well based at least in part on the respective fill height of sample within each sample-containing well;
    acquiring, using the focal plane height determined for each sample-containing well, successive images of the respective sample-containing wells;
    determining, using the acquired successive images, a change in a measured optical parameter at each sample-containing well over time relative to a baseline; and
    generating an assessment of micro-organism presence within the sample based on the determined changes in the measured optical parameter at each sample-containing well over time.

11. The method of claim 10, wherein partitioning the sample between the plurality of wells comprises the steps of:
    loading the sample through an inlet into a sealed environment comprising the well plate and a compliant layer positioned above the plurality of wells of the well plate, wherein the sample, when loaded, flows through a plurality of mesofluidic channels fluidically connecting the wells of the well plate so as to partition the sample between the plurality of wells; and
    applying pressure to the compliant layer so as to seal the plurality of wells after the sample is loaded.

12. The method of claim 10, wherein measuring the fill height of each sample-containing well comprises:
    scanning through each sample-containing well using a laser to generate laser scan plots for each sample-containing well; and
    identifying peaks associated with the changes in indices of refraction indicative of a bottom of the well plate and height of the fluid column within each respective sample-containing well.

13. The method of claim 10, comprising:
    determining a volume of sample within each sample-containing well using the respective fill heights.

14. The method of claim 13, wherein the volume of sample within each sample-containing well is determined using the fill height for a respective sample containing well and a known geometry of the wells of the well plate.

15. The method of claim 14, wherein the assessment of microorganism presence within the sample is based at least in part on the volume of sample within each sample-containing well.

16. The method of claim 15, wherein the quantification of bio-burden comprises a most-probable number determination based on a number of sample-containing wells exhibiting micro-organism growth relative to the baseline.

17. A method for assessing analyzing a well plate, comprising:
   partitioning a sample between a plurality of wells of a well plate to form a plurality of sample-containing wells;
   measuring a fill height of each sample-containing well of the plurality of sample-containing;
   generating an assessment of micro-organism presence within the sample based on images acquired over time of the sample-containing wells at, for each sample containing well, a respective focal plane height determined based at least in part on the respective fill height of each sample-containing well.

18. The method of claim 17, wherein measuring the fill height of each sample-containing well comprises:
   scanning through each sample-containing well using a laser to generate laser scan plots for each sample-containing well; and
   identifying peaks associated with the changes in indices of refraction indicative of a bottom of the well plate and height of the fluid column within each respective sample-containing well.

19. The method of claim 17, comprising:
   determining a volume of sample within each sample-containing well using the fill height for each respective sample-containing well and a known geometry of the wells of the well plate.

20. The method of claim 19, wherein the assessment of microorganism presence within the sample is based at least in part on the volume of sample within each sample-containing well.

* * * * *